United States Patent
Navarro et al.

(10) Patent No.: US 7,794,499 B2
(45) Date of Patent: Sep. 14, 2010

(54) PROSTHETIC INTERVERTEBRAL SPINAL DISC WITH INTEGRAL MICROPROCESSOR

(75) Inventors: Richard Robert Navarro, Hinckley, OH (US); Christopher Paul Cole, Stow, OH (US); Randall Raymond Theken, Barberton, OH (US)

(73) Assignee: Theken Disc, L.L.C., Akron, OH (US)

( * ) Notice: Subject to any disclaimer, the term of this patent is extended or adjusted under 35 U.S.C. 154(b) by 1169 days.

(21) Appl. No.: 10/863,858

(22) Filed: Jun. 8, 2004

(65) Prior Publication Data
US 2005/0273170 A1   Dec. 8, 2005

(51) Int. Cl.
*A61F 2/44* (2006.01)
*A61B 5/03* (2006.01)

(52) U.S. Cl. .......... 623/17.11; 600/594; 600/300; 600/301; 623/914

(58) Field of Classification Search ... 623/17.11–17.16, 623/914; 600/594
See application file for complete search history.

(56) References Cited

U.S. PATENT DOCUMENTS

| | | | |
|---|---|---|---|
| 3,662,758 A | 5/1972 | Glover | |
| 3,699,970 A | 10/1972 | Brindley et al. | |
| 3,944,982 A | 3/1976 | Mogi et al. | |
| 4,057,069 A | 11/1977 | Dorffer et al. | |
| 4,220,156 A | 9/1980 | Schulman et al. | |
| 4,284,856 A | 8/1981 | Hochmair et al. | |
| 4,333,072 A | 6/1982 | Beigel | |
| 4,357,497 A | 11/1982 | Hochmair et al. | |
| 4,408,608 A | 10/1983 | Daly et al. | |
| 4,459,989 A | 7/1984 | Borkan | |
| 4,515,158 A | 5/1985 | Patrick et al. | |
| 4,592,359 A | 6/1986 | Galbraith | |
| 4,592,360 A | 6/1986 | Lesnick | |
| 4,602,638 A | 7/1986 | Adams | |
| 4,612,934 A | 9/1986 | Borkan | |
| 4,679,560 A | 7/1987 | Galbraith | |
| 4,712,179 A | 12/1987 | Heimer | |

(Continued)

FOREIGN PATENT DOCUMENTS

EP  0 619 101 A1  10/1994

(Continued)

OTHER PUBLICATIONS

Bao and Yuan; "Artificial Disc Technology"; Neurosurg Focus 9(4), 2000; American Association of Neurological Surgeons; From: www.medscape.com.

(Continued)

*Primary Examiner*—Eduardo C Robert
*Assistant Examiner*—Ellen C. Hammond
(74) *Attorney, Agent, or Firm*—Howison & Arnott, L.L.P.

(57) ABSTRACT

A device for storing data related to movement of a prosthetic implant includes at least one transducer for generating at least one real time movement signal responsive to movement within the prosthetic implant. A processor generates movement data parameters and associated time stamps in response to the real time movement signal. The generated data parameters and time stamps are stored within a memory associated with the processor. A communications link may be used to selectively access the movement data parameters and the time stamps in the memory from an external source.

47 Claims, 9 Drawing Sheets

U.S. PATENT DOCUMENTS

| | | |
|---|---|---|
| 4,735,204 A | 4/1988 | Sussman et al. |
| 4,793,353 A | 12/1988 | Borkan |
| 4,867,164 A | 9/1989 | Zabara |
| 4,947,844 A | 8/1990 | McDermott |
| 4,979,508 A | 12/1990 | Beck |
| 5,117,825 A | 6/1992 | Grevious |
| 5,170,806 A | 12/1992 | Colen |
| 5,186,170 A | 2/1993 | Varrichio et al. |
| 5,197,488 A * | 3/1993 | Kovacevic ................. 600/595 |
| 5,235,980 A | 8/1993 | Varrichio et al. |
| 5,300,120 A | 4/1994 | Knapp et al. |
| 5,313,953 A | 5/1994 | Yomtov et al. |
| 5,314,453 A | 5/1994 | Jeutter |
| 5,314,457 A | 5/1994 | Jeutter et al. |
| 5,314,458 A | 5/1994 | Najafi et al. |
| 5,321,618 A | 6/1994 | Gessman |
| 5,324,315 A | 6/1994 | Grevious |
| 5,326,363 A | 7/1994 | Aikins |
| 5,350,411 A | 9/1994 | Ryan et al. |
| 5,360,437 A | 11/1994 | Thompson |
| 5,370,666 A | 12/1994 | Lindberg et al. |
| 5,383,912 A | 1/1995 | Cox et al. |
| 5,383,915 A | 1/1995 | Adams |
| 5,405,367 A | 4/1995 | Schulman et al. |
| 5,411,536 A | 5/1995 | Armstrong |
| 5,433,736 A | 7/1995 | Nilsson |
| 5,439,481 A | 8/1995 | Adams |
| 5,456,724 A | 10/1995 | Yen et al. |
| 5,522,865 A | 6/1996 | Schulman et al. |
| 5,522,866 A | 6/1996 | Fernald |
| 5,545,191 A | 8/1996 | Mann et al. |
| 5,562,713 A | 10/1996 | Silvian |
| 5,562,714 A | 10/1996 | Grevious |
| 5,569,307 A | 10/1996 | Schulman et al. |
| 5,579,781 A | 12/1996 | Cooke |
| 5,584,870 A | 12/1996 | Single et al. |
| 5,593,430 A | 1/1997 | Renger |
| 5,626,625 A | 5/1997 | Fernald |
| 5,626,630 A | 5/1997 | Markowitz et al. |
| 5,630,835 A | 5/1997 | Brownlee |
| 5,630,836 A | 5/1997 | Prem et al. |
| 5,662,694 A | 9/1997 | Lidman et al. |
| 5,674,249 A | 10/1997 | de Coriolis et al. |
| 5,674,265 A | 10/1997 | Deschamps et al. |
| 5,683,432 A | 11/1997 | Goedeke et al. |
| 5,697,958 A | 12/1997 | Paul et al. |
| 5,703,474 A | 12/1997 | Smalser |
| 5,720,770 A | 2/1998 | Nappholz et al. |
| 5,720,771 A | 2/1998 | Snell |
| 5,728,154 A | 3/1998 | Crossett et al. |
| 5,733,313 A | 3/1998 | Barreras et al. |
| 5,735,887 A | 4/1998 | Barreras et al. |
| 5,741,314 A | 4/1998 | Daly et al. |
| 5,741,315 A | 4/1998 | Lee et al. |
| 5,759,199 A | 6/1998 | Snell et al. |
| 5,766,232 A | 6/1998 | Grevious et al. |
| 5,769,876 A | 6/1998 | Silvian |
| 5,776,171 A | 7/1998 | Peckham et al. |
| 5,792,207 A | 8/1998 | Dietrich |
| 5,792,208 A | 8/1998 | Gray |
| 5,814,089 A | 9/1998 | Stokes et al. |
| 5,833,603 A | 11/1998 | Kovacs et al. |
| 5,836,983 A | 11/1998 | Weijand et al. |
| 5,843,139 A | 12/1998 | Goedeke et al. |
| 5,861,018 A | 1/1999 | Feierbach |
| 5,861,019 A | 1/1999 | Sun et al. |
| 5,891,184 A | 4/1999 | Lee et al. |
| 5,893,889 A * | 4/1999 | Harrington ............... 623/17.16 |
| 5,899,928 A | 5/1999 | Sholder et al. |
| 5,899,931 A | 5/1999 | Deschamp et al. |
| 5,919,214 A | 7/1999 | Ciciarelli et al. |
| 5,935,078 A | 8/1999 | Feierbach |
| 5,935,171 A | 8/1999 | Schneider et al. |
| 5,941,906 A | 8/1999 | Barreras et al. |
| 5,951,594 A | 9/1999 | Kerver |
| 5,961,540 A | 10/1999 | Renger |
| 5,977,431 A | 11/1999 | Knapp |
| 5,978,713 A | 11/1999 | Prutchi et al. |
| 5,991,664 A | 11/1999 | Seligman |
| 5,999,848 A | 12/1999 | Gord et al. |
| 5,999,857 A | 12/1999 | Weijand et al. |
| 6,009,350 A | 12/1999 | Renken |
| 6,034,296 A | 3/2000 | Elvin et al. |
| 6,047,214 A | 4/2000 | Mueller et al. |
| 6,058,330 A | 5/2000 | Borza |
| 6,059,784 A | 5/2000 | Perusek |
| 6,070,103 A | 5/2000 | Ogden |
| 6,073,050 A | 6/2000 | Griffith |
| 6,076,016 A | 6/2000 | Feierbach |
| 6,083,248 A | 7/2000 | Thompson |
| 6,106,551 A | 8/2000 | Crossett et al. |
| 6,115,636 A | 9/2000 | Ryan |
| 6,141,592 A | 10/2000 | Pauly |
| 6,167,310 A | 12/2000 | Grevious |
| 6,167,312 A | 12/2000 | Goedeke |
| 6,169,925 B1 | 1/2001 | Villaseca et al. |
| 6,176,879 B1 | 1/2001 | Reischl et al. |
| 6,185,452 B1 | 2/2001 | Schulman et al. |
| 6,201,993 B1 | 3/2001 | Kruse et al. |
| 6,223,083 B1 | 4/2001 | Rosar |
| 6,228,085 B1 | 5/2001 | Theken et al. |
| 6,230,059 B1 | 5/2001 | Duffin |
| 6,236,889 B1 | 5/2001 | Soykan et al. |
| 6,239,724 B1 | 5/2001 | Doron et al. |
| 6,240,317 B1 | 5/2001 | Villaseca et al. |
| 6,243,608 B1 | 6/2001 | Pauly et al. |
| 6,245,109 B1 | 6/2001 | Mendes et al. |
| 6,249,703 B1 | 6/2001 | Stanton et al. |
| 6,263,245 B1 | 7/2001 | Snell |
| 6,263,246 B1 | 7/2001 | Goedeke et al. |
| 6,263,247 B1 | 7/2001 | Mueller et al. |
| 6,295,473 B1 | 9/2001 | Rosar |
| 6,298,271 B1 | 10/2001 | Weijand |
| 6,301,504 B1 | 10/2001 | Silvian |
| 6,325,756 B1 | 12/2001 | Webb et al. |
| 6,345,203 B1 | 2/2002 | Mueller et al. |
| 6,348,070 B1 | 2/2002 | Teissl et al. |
| 6,349,234 B2 | 2/2002 | Pauly et al. |
| 6,356,789 B1 | 3/2002 | Hinssen et al. |
| 6,358,202 B1 | 3/2002 | Arent |
| 6,389,318 B1 | 5/2002 | Zarinetchi et al. |
| 6,400,990 B1 | 6/2002 | Silvian |
| 6,405,088 B1 | 6/2002 | Merlin et al. |
| 6,424,867 B1 | 7/2002 | Snell et al. |
| 6,427,088 B1 | 7/2002 | Bowman et al. |
| 6,430,444 B1 | 8/2002 | Borza |
| 6,434,429 B1 | 8/2002 | Kraus et al. |
| 6,441,747 B1 | 8/2002 | Khair et al. |
| 6,442,433 B1 | 8/2002 | Linberg |
| 6,443,891 B1 | 9/2002 | Grevious |
| 6,447,448 B1 * | 9/2002 | Ishikawa et al. ............ 600/300 |
| 6,453,200 B1 | 9/2002 | Koslar |
| 6,456,256 B1 | 9/2002 | Amundson et al. |
| 6,456,875 B1 | 9/2002 | Wilkinson et al. |
| 6,456,883 B1 | 9/2002 | Torgerson et al. |
| 6,456,887 B1 | 9/2002 | Dudding et al. |
| 6,463,329 B1 | 10/2002 | Goedeke |
| 6,470,213 B1 | 10/2002 | Alley |
| 6,470,215 B1 | 10/2002 | Kraus et al. |
| 6,471,645 B1 | 10/2002 | Warkentin et al. |
| 6,473,652 B1 | 10/2002 | Sarwal et al. |
| 6,477,424 B1 | 11/2002 | Thompson et al. |
| 6,477,425 B1 | 11/2002 | Norwick et al. |
| 6,478,737 B2 | 11/2002 | Bardy |

| | | | | | | |
|---|---|---|---|---|---|---|
| 6,480,744 | B2 | 11/2002 | Ferek-Petric | 2002/0103514 A1 | 8/2002 | Abrahamson |
| 6,480,745 | B2 | 11/2002 | Nelson et al. | 2002/0107557 A1 | 8/2002 | Edell et al. |
| 6,487,452 | B2 | 11/2002 | Legay | 2002/0120310 A1 | 8/2002 | Linden et al. |
| 6,490,487 | B1 | 12/2002 | Kraus et al. | 2002/0123776 A1 | 9/2002 | Von Arx et al. |
| 6,505,072 | B1 | 1/2003 | Linder et al. | 2002/0123777 A1 | 9/2002 | Dolgin et al. |
| 6,505,409 | B2 | 1/2003 | Toda et al. | 2002/0123778 A1 | 9/2002 | Linberg |
| 6,507,759 | B1 | 1/2003 | Prutchi et al. | 2002/0123779 A1 | 9/2002 | Zarinetchi et al. |
| 6,510,345 | B1 | 1/2003 | Van Bentem | 2002/0169487 A1 | 11/2002 | Graindorge |
| 6,522,928 | B2 | 2/2003 | Whitehurst et al. | 2002/0169488 A1 | 11/2002 | Limousin et al. |
| 6,530,954 | B1 | 3/2003 | Eckmiller | 2002/0173830 A1 | 11/2002 | Starkweather et al. |
| 6,535,766 | B1 | 3/2003 | Thompson et al. | 2002/0183806 A1 | 12/2002 | Abrahamson et al. |
| 6,539,253 | B2 | 3/2003 | Thompson et al. | 2002/0193846 A1 | 12/2002 | Pool et al. |
| 6,542,777 | B1 | 4/2003 | Griffith et al. | 2002/0193847 A1 | 12/2002 | Daum et al. |
| 6,553,262 | B1 | 4/2003 | Lang et al. | 2003/0009203 A1 | 1/2003 | Lebel et al. |
| 6,554,781 | B1* | 4/2003 | Hill et al. .................... 600/594 | 2003/0009204 A1 | 1/2003 | Amundson et al. |
| 6,556,871 | B2 | 4/2003 | Schmitt et al. | 2003/0014090 A1 | 1/2003 | Abrahamson |
| 6,561,975 | B1 | 5/2003 | Pool et al. | 2003/0018369 A1 | 1/2003 | Thompson et al. |
| 6,564,104 | B2 | 5/2003 | Nelson et al. | 2003/0028226 A1 | 2/2003 | Thompson et al. |
| 6,564,105 | B2 | 5/2003 | Starkweather et al. | 2003/0032993 A1 | 2/2003 | Mickle et al. |
| 6,567,703 | B1 | 5/2003 | Thompson et al. | 2003/0040806 A1 | 2/2003 | MacDonald |
| 6,571,128 | B2 | 5/2003 | Lebel et al. | 2003/0045913 A1 | 3/2003 | Stroebel et al. |
| 6,574,503 | B2 | 6/2003 | Ferek-Petric | 2003/0050676 A1 | 3/2003 | Hubelbank et al. |
| 6,574,509 | B1 | 6/2003 | Kraus et al. | 2003/0060859 A1 | 3/2003 | Bourget |
| 6,574,510 | B2 | 6/2003 | Von Arx et al. | 2003/0065370 A1 | 4/2003 | Lebel et al. |
| 6,574,511 | B2 | 6/2003 | Lee | 2003/0069614 A1 | 4/2003 | Bowman et al. |
| 6,577,898 | B2 | 6/2003 | Silvian | 2003/0069644 A1 | 4/2003 | Kovacevic et al. |
| 6,577,899 | B2 | 6/2003 | Lebel et al. | 2003/0074035 A1 | 4/2003 | Bornhoft et al. |
| 6,577,900 | B1 | 6/2003 | Silvian | 2003/0074036 A1 | 4/2003 | Prutchi et al. |
| 6,577,901 | B2 | 6/2003 | Thompson | 2003/0083718 A1 | 5/2003 | Cox |
| 6,580,177 | B1 | 6/2003 | Hagood, IV et al. | 2003/0083719 A1 | 5/2003 | Shankar et al. |
| 6,580,947 | B1 | 6/2003 | Thompson | 2003/0088295 A1 | 5/2003 | Cox |
| 6,580,948 | B2 | 6/2003 | Haupert et al. | 2003/0114896 A1 | 6/2003 | Boute et al. |
| 6,585,763 | B1 | 7/2003 | Keilman et al. | 2003/0114897 A1 | 6/2003 | Von Arx et al. |
| 6,655,035 | B2 | 12/2003 | Ghandi et al. | 2003/0114898 A1 | 6/2003 | Von Arx et al. |
| 6,662,048 | B2 | 12/2003 | Balczewski et al. | 2003/0114899 A1 | 6/2003 | Woods et al. |
| 6,706,005 | B2 | 3/2004 | Roy et al. | 2003/0225440 A1 | 12/2003 | Cancel et al. |
| 6,731,976 | B2 | 5/2004 | Penn et al. | 2005/0234555 A1* | 10/2005 | Sutton et al. .............. 623/17.15 |
| 6,802,811 | B1 | 10/2004 | Slepian | | | |
| 6,834,436 | B2 | 12/2004 | Townsend et al. | | | |
| 7,169,181 | B2* | 1/2007 | Kuras ..................... 623/17.11 | | | |
| 7,531,002 | B2* | 5/2009 | Sutton et al. ............. 623/17.15 | WO | WO 97/33513 | 9/1997 |
| 2001/0023360 | A1 | 9/2001 | Nelson et al. | | | |
| 2001/0023361 | A1 | 9/2001 | Pauly et al. | | | |
| 2001/0027331 | A1 | 10/2001 | Thompson | | | |
| 2001/0031998 | A1 | 10/2001 | Nelson et al. | | | |
| 2001/0041920 | A1 | 11/2001 | Starkweather et al. | | | |
| 2002/0013613 | A1 | 1/2002 | Haller et al. | | | |
| 2002/0013614 | A1 | 1/2002 | Thompson | | | |
| 2002/0026224 | A1 | 2/2002 | Thompson et al. | | | |
| 2002/0032470 | A1 | 3/2002 | Linberg | | | |
| 2002/0042637 | A1 | 4/2002 | Stover | | | |
| 2002/0045920 | A1 | 4/2002 | Thompson | | | |
| 2002/0049394 | A1* | 4/2002 | Roy et al. .................... 600/594 | | | |
| 2002/0049480 | A1 | 4/2002 | Lebel et al. | | | |
| 2002/0049481 | A1 | 4/2002 | Conley et al. | | | |
| 2002/0049482 | A1 | 4/2002 | Fabian et al. | | | |
| 2002/0062141 | A1 | 5/2002 | Moore | | | |
| 2002/0065539 | A1 | 5/2002 | Von Arx et al. | | | |
| 2002/0065540 | A1 | 5/2002 | Lebel et al. | | | |
| 2002/0068962 | A1 | 6/2002 | Ferek-Petric | | | |
| 2002/0072733 | A1 | 6/2002 | Flaherty | | | |
| 2002/0072783 | A1 | 6/2002 | Goedeke et al. | | | |
| 2002/0072784 | A1 | 6/2002 | Sheppard et al. | | | |
| 2002/0072785 | A1 | 6/2002 | Nelson et al. | | | |
| 2002/0077671 | A1 | 6/2002 | Govari et al. | | | |
| 2002/0077672 | A1 | 6/2002 | Govari et al. | | | |
| 2002/0077673 | A1 | 6/2002 | Penner et al. | | | |
| 2002/0082665 | A1 | 6/2002 | Haller et al. | | | |
| 2002/0087203 | A1 | 7/2002 | Schmitt et al. | | | |
| 2002/0095195 | A1 | 7/2002 | Mass et al. | | | |
| 2002/0095196 | A1 | 7/2002 | Linberg | | | |
| 2002/0099423 | A1 | 7/2002 | Berg et al. | | | |
| 2002/0099424 | A1 | 7/2002 | Ferek-Petric | | | |

FOREIGN PATENT DOCUMENTS

OTHER PUBLICATIONS

VTI Technologies; SCA610 Series Specification; Rev. May 5, 2003.
Texas Instruments; Mixed Signal Microcontroller Data Sheet; Jul. 2000, Rev. Aug. 2003.
CYGNAL; Enginering Drafts; Sep. 2, 2003.
Silicon Laboratories; "Wireless Digital Full-Duplex Voice Tansceiver"; Rev. 1.1, Dec. 2003.
Hodge, W. A., et al., Contact Pressures in the Human Hip Joint Measured In Vivo, Proc. Natl. Acad. Sci., Biophysics, May 1986, pp. 2879-2883, vol. 83, USA.
Carlson, Charles Elwood, Measurement of Pressure Distribution in the Human Hip Joint; Thesis, Jun. 1967, pp. i-vi and 1-49; Massachusetts Institute of Technology; Cambridge, Massachusetts.
Carlson, Charles E., An Instrumented Prosthesis for Measuring the Cartilage Surface Pressure Distribution in the Human Hip; Thesis, Jun. 1972, pp. 1-185; Massachusetts Institute of Technology; Cambridge, Massachusetts.
Carlson, Charles E., et al.; A Radio Telemetry Device for Monitoring Cartilage Surface Pressures in the Human Hip; Jul. 1974; pp. 257-264; Transactions on Biomedical Engineering, vol. BME-21, No. 4, IEEE, USA.
Carlson, Charles E, et al.; "A Look at the Prosthesis-Cartilage Interface: Design of a Hip Prosthesis Containing Pressure Transducers"; J Biomed Mater Res Symposium, No. 5 (Part 2), 1974; pp. 261-269; USA.
Flick, Bernd B., "A Portable Microsystem-Baed Telemetric Pressure and Temperature Measurement Unit," IEEE Transactions on Biomedical Engineering, vol. 47, No. 1, pp. 12-16, Jan. 2000.
Rohlmann, A. et al., "Comparison of loads on internal spinal fixation devices measured in vitro and in vivo," Med Eng. Phys., vol. 19, No. 6, pp. 539-546, Apr. 1997.

Chatzandroulis, Stavros et al., "A Miniature Pressure System with a Capacitive Sensor and a Passive Telemetry Link for Use in Implantable Applications," Journal of Microelectromechanical Systems, vol. 9, No. 1, pp. 18-23, March 2000.

Mehregany M. et al., "Introduction to Mems," Microengineering Aerospace Systems, Chapter 1, pp. 1-28, 1999.

Ledet MS, Eric H, et al., "Real-Time In Vivo Loading in the Lumbar Spine," Spine, vol. 25, No. 20, pp. 2595-2600, Apr. 2000.

* cited by examiner

PROSTHETIC INTERVERTEBRAL SPINAL DISC WITH INTEGRAL MICROPROCESSOR

TECHNICAL FIELD OF THE INVENTION

This invention relates to an artificial, constrained motion spinal disc for replacing intervertebral discs in the lower back, and more particularly, to an artificial disc including processing and memory storage capabilities.

BACKGROUND OF THE INVENTION

The human spine is composed of many vertebra stacked one upon the other, with an intervertebral disc between each pair of adjacent vertebra. The discs act as cartilaginous cushions and shock absorbers. The spinal cord runs in a bony canal formed by successive openings in these bones. The spinal nerves exit the spinal cord between pairs of vertebrae and supply nerves and nerve signals to and from other body structures.

The vertebral disc is a complex joint both anatomically and functionally. It is composed of three component structures: the nucleus pulposus; the annulus fibrosis, and the vertebral end plates. The biomedical composition and anatomical arrangements within these component structures are related to the biomechanical function of the disc.

The nucleus pulposus, occupying about 24% to 40% of the total disc cross-sectional area, usually contains approximately 70% to 90% water by weight.

The annulus fibrosis is a concentrically laminated structure which contains highly aligned collagen fibers and fibril cartilage embedded in an amorphous round substance. The annular layers are oriented at approximately +/−60° to the longitudinal axis of the spine. The annulus fibrosis usually contains approximately eight to ten layers and is mechanically the main stabilizing structure which resists torsional and bending forces applied to the disc.

The two vertebral end plates separate the disc from the adjacent vertebral bodies, and are composed of hyaline cartilage.

Spinal discs may be damaged or displaced due to trauma or disease. In either case, the nucleus pulposus may herniate and protrude into the vertebral canal or intervertebral foramen. This condition is known as a herniated or "slipped" disc. This may in turn press upon the spinal nerve that exits the vertebral canal through the partially obstructed foramen, causing pain or paralysis in the area of its distribution. The most frequent site of occurrence of a herniated disc is in the lower lumbar region. To alleviate this condition, two procedures are common.

First, it may be necessary to remove the involved disc surgically and fuse the two adjacent vertebrae together. Spinal fusion is a good method of eliminating symptoms, but at the expense of total loss of motion of the fused vertebral joint, as well as increased stress in the adjacent segments. In many long term patients of fused spinal segments, a detrimental phenomena has been observed whereby discs adjacent to the fused spinal segment will have increased motion and stress due to the increased stiffness of the fused segment. This is sometimes referred to "cascading spine syndrome," where previously normal motion segments above or below a fused segment exhibit spondylolisthesis, or degenerative disc disease due to increased loading. A second method for alleviating disc problems is insertion of an intervertebral disc replacement. The object of an intervertebral disc replacement is to provide a prosthetic disc that combines both stability to support high loads of patient vertebrae and flexibility to provide the patient with sufficient mobility and proper spinal column load distribution. In attempting to satisfy these competing design requirements, basically four types of intervertebral discs have been developed; elastomer disc, ball and socket disc, mechanical spring disc, and hybrid discs.

No matter which of the artificial intervertebral disc replacements are used, all lack memory storage and processing capabilities that would assist a doctor in diagnosing a patient's spinal condition and the performance of the artificial disc once implanted. Once the artificial disc is inserted into the patient's spine, the doctor is required to rely upon verbal feedback and imaging techniques from the patient in order to diagnose any problems that may be occurring with respect to the artificial disc. This type of feedback is limited due to the lack of ability of the patient to properly describe sensations or feelings which may be coming from their back, and may further be limited by a lack of candor on the part of the patient who may fail to tell the doctor about activities the patient has engaged in that are not appropriate for the artificial disc. Thus, there is a need for a type of artificial intervertebral disc that provides processing and memory storage capabilities that would assist in the collection of data relating to the intervertebral disc that could be used either output in real time to a doctor diagnosing a patient, or alternatively, could be downloaded from the memory to provide information as to the patient's load history.

SUMMARY OF THE INVENTION

The present invention overcomes the foregoing and other problems with an apparatus for storing data relating to an event in a prosthetic prosthetic implant. A prosthetic prosthetic implant located within a joint of a patient's body includes at least one transducer for generating a real time event signal responsive to an event within the prosthetic joint. The real time event signals from the transducer are input to a processor. The processor generates movement data parameters from the real time event signals and also generates a time stamp indicating the point in time the real time event signals were generated by the transducers. The event data parameters and time stamps are stored within a memory associated with the processor. The event data parameters and time stamps may be selectively accessed in the memory from an external source via a communications link.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
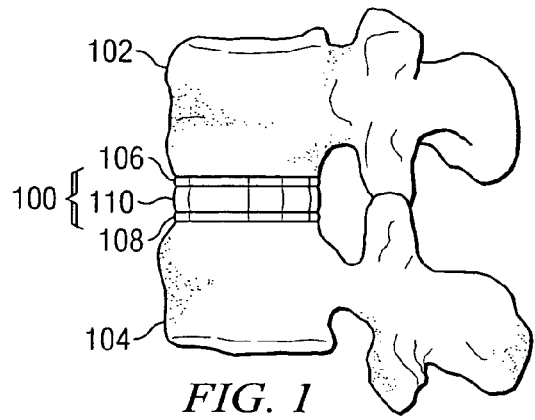
FIG. 1 illustrates an artificial disc between two vertebrae of the spinal column.

While the system is described with respect to an artificial intervertebral disc, it should be realized that the described system would be useful in providing diagnostic information to a doctor with respect to any artificial joint which may be placed within the human body, wherein information regarding specific loads in joints during activity is desired. Referring now to the drawings, and more particularly to FIG. 1, there is illustrated placement of an artificial disc 100 between a first vertebra 102 and a second vertebra 104 of an individual's spinal column. As can be seen in FIG. 1, the artificial disc 100 rests in the space between the vertebrae 102 and 104 where the disc of an individual's spine normally resides. The artificial disc 100 consists of an upper plate 106 and a lower plate 108 including an elastomeric layer 110 disposed between the upper and lower plates. This will allow all forces associated with the spine to be transferred to the upper and lower plates 106 and 108.

Figure 2:
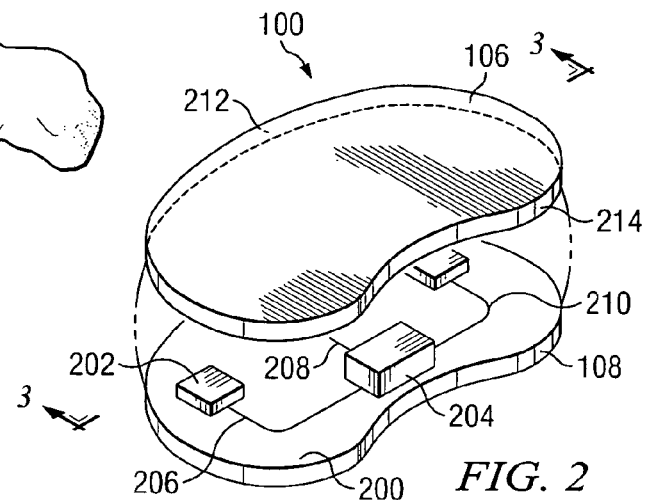
FIG. 2 is a perspective view of the artificial disc.

Referring now to FIG. 2, there is illustrated a perspective view of the artificial disc 100 consisting of the upper plate 106 and the lower plate 108. For purposes of illustration, the elastomeric layer 100 has been removed and only the edges thereof are shown in phantom. The electronics portion of the artificial disc 100 is located on the upper surface 200 of the lower plate 108. The electronics portion consists of a plurality of transducers 202, one of which is illustrated in FIG. 2. The transducers 202 are connected via electrical line 206 to circuitry within a lower projection 204. The circuitry is within the interior of the lower projection 204 and comprises the processor and memory portions of the artificial disc 100. Additional transducers are connected via lines 208 and 210. As can be seen in FIG. 2, each of the upper plate 100 and the lower plate 108 has a substantially concave shaped back edge 212 and a convex shaped front edge 214. Of course designs of other shapes would also be applicable. The upper plate 106 and lower plate 108 are formed to substantially conform to the shape of the vertebra 102 and vertebra 104 between which the artificial disc 100 is fitted within the spinal column of a patient.

Figure 3:
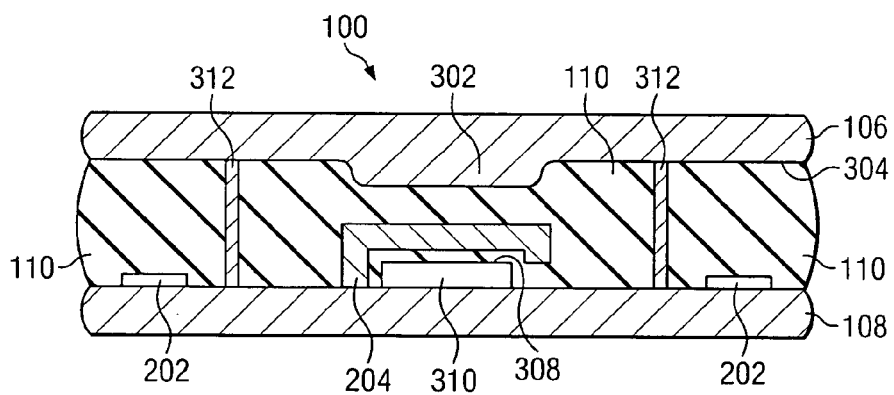
FIG. 3 is a cross-sectional view along line 3-3 illustrated in FIG. 2 of the artificial disc.

Referring now to FIG. 3, there is illustrated a cross-sectional view of the artificial disc 100 along section line 3-3 indicated in FIG. 2. Upper plate 106 rests on elastomeric layer 110 and lower plate 108 is below the elastomeric layer 110. Upper projection 302 extends downwardly from the bottom surface 304 of upper plate 106. As described previously with respect to FIG. 2, lower projection 204 extends upwardly from the upper surface 200 of lower plate 308. The lower plate 308 also contains the electronics package 310 associated with the artificial disc 100. Also running through the elastic layer 100 are restraining members 312 which prevent upper plate 106 and lower plate 108 from separating by greater than a maximum allowable distance. Upper projection 302 and lower projection 204 provide stops for preventing upper plate 106 and lower plate 108 from compressing toward each other beyond a minimum allowable distance.

Figure 4:
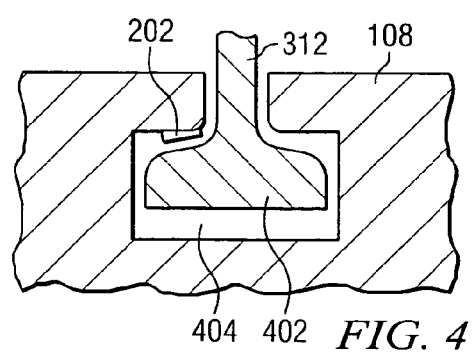
FIG. 4 illustrates the placement of a transducer near a motion limiting member of the artificial disc.

Referring now also to FIG. 4, there is illustrated the end portion 402 of one of the restraining members 312 within the lower plate 108. The lower plate 108 defines a chamber 404 for containing the end portion 402 of the restraining member 312. When the end portion 402 of restraining member 312 moves to the upper portion of chamber 404, the end portion 402 will activate a transducer 406 on the upper edge of chamber 404. Activation of the transducer 406 provides a signal to the electronics package 310 on the lower plate 108 of the artificial disc 100. This generates and stores data indicating that the restraining member 312 has restrained plate 108 from exceeding its maximum allowable distance with respect to upper plate 106. In a similar manner, additional transducers 406 could be placed proximate to opposite ends of the restraining member 312 to produce similar transducer outputs defining forces applied to the restraining members 312.

Figure 4A:
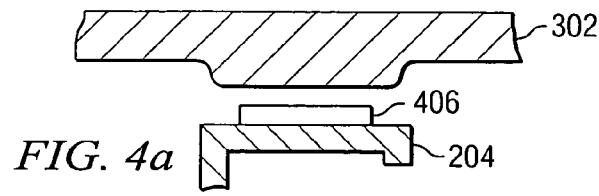

Referring now to FIG. 4a, there is illustrated the compression stop mechanism consisting of the upper projection 302 and the lower projection 204. The upper projection 302 and lower projection 204 work in concert to prevent the upper plate 106 and lower plate 108 from compressing beyond a certain point. Compression is prevented by the upper projection 302 coming into contact with lower projection 204. A transducer 406 placed between the upper projection 302 and lower projection 204 would provide an indication of the forces acting between the two projections. Activation of the transducer 406 provides a signal to the electronics package 310 on the lower plate 108 of the artificial disc 100. This generates and stores data indicating that the upper projection 302 and the lower projection 204 have restrained plates 106 and 108 from exceeding their maximum allowable compression distance.

Figure 5:
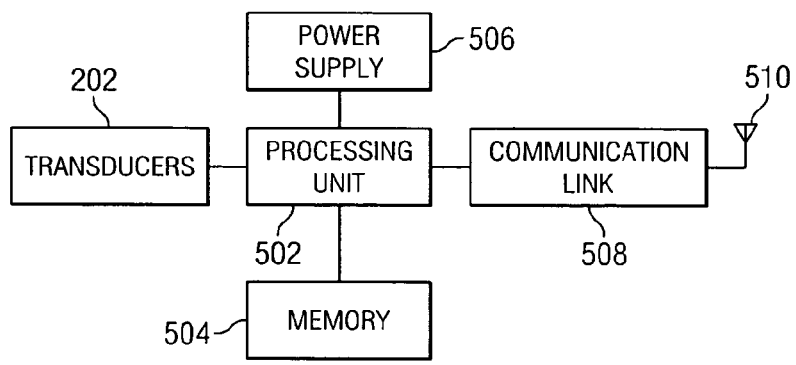
FIG. 5 is a functional block diagram of the electronics associated with the artificial disc.

Referring now to FIG. 5, there is illustrated a general block diagram of the electronics package 310 and transducers 202 used within the artificial disc 100. A number of transducers 202 provide inputs to a processing unit 502. The transducers 202 comprise piezoelectric devices that generate a voltage in response to mechanical forces being applied to the transducers caused by movements between the upper plate 106 and lower plate 108. These transducers 202 are able to measure compressive forces in the artificial disc 100. In addition to the piezoelectric transducers, the transducers 202 may include one or more accelerometer/inclinometer sensors for enabling acceleration and inclination measurements in the sagital and coronal planes. In one embodiment, the accelerometer/inclinometer sensor may comprise the VTI Technologies SCA610 series device. The transducers 202 utilized by the artificial disc 100 may also include a temperature sensor for providing local temperature information related to the artificial disc 100. The transducers enable the measurement of static data, dynamic data and positional data with respect to movement within the artificial disc 100 and distributed there across, in addition to measurements of temperature.

The processing unit 502 processes the received transducer data and may either output the data in real time or store parameters representative of the data within a memory 504 associated with the processing unit 502. The processing unit 502 may consist of any number of known microprocessing units including one of the TI MSP430 family of processors. The memory 504 comprises a flash memory or RAM for storing the parameters relating to the outputs of the transducers 202. Communications link 508 and antenna 510 are provided to generate a wireless communications link between the electronics package 310 of the artificial disc and an external processing functionality. In this way, data can be uploaded from the artificial disc in one of two fashions.

In a real time mode, outputs of the transducers 202 are processed and output in real time from the processing unit 502 using the communications link 508 over antenna 510. In an upload mode, time stamped parameters stored within the memory 504 are uploaded by the processing unit 502 to the external source using the communications link 508 and antenna 510. The upload mode has the advantage of providing data relating to user activities and the activities effect upon the artificial disc 100 over a wide period of time including times when the patient may not be present within a doctor's office. The processing unit 502, communications link 508, memory 504 and transducers 202 are powered by a local power supply 506 which may consist of, for example, a battery, which battery may be rechargeable. The local power supply 506 may also consist of inductively coupled power or piezoelectric power generation.

Figure 6:
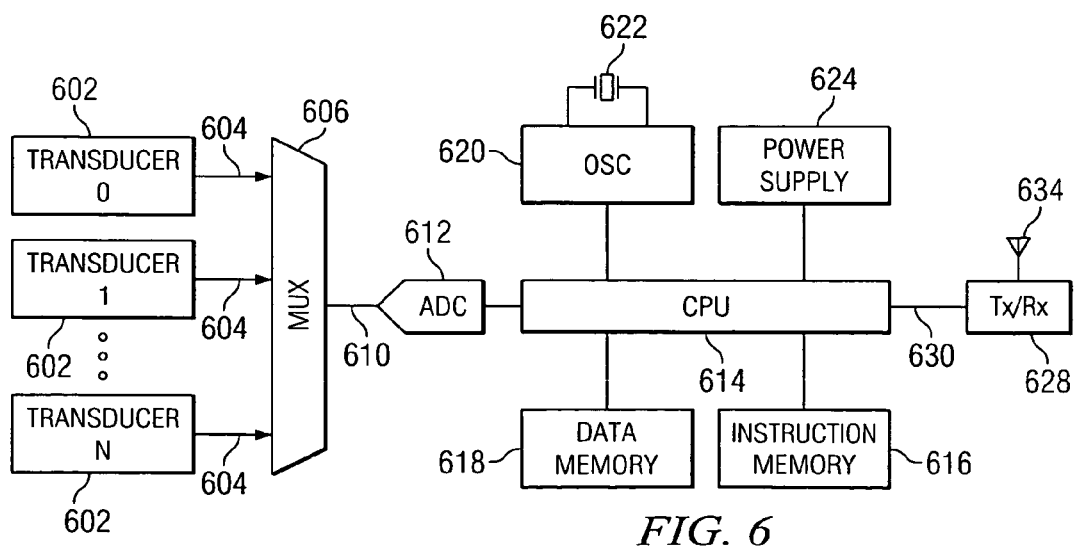
FIG. 6 is a detailed block diagram of the electronics of the artificial disc.

Referring now to FIG. 6, there is illustrated a generalized block diagram of the processing unit 502. As noted herein above, there are provided a plurality of transducers 202, they being indicated as a plurality of transducers 602 labeled XDUCER 0, XDUCER 1, . . . , XDUCER N. These transducers 602 can be any type of transducer that provides an analog output on analog output line 604, a separate analog line 604 associated with each of the transducers 602. However, the transducers can provide any type of output, such as digital. The analog lines 604 are input to a multiple input multiplexer 606 (MUX) which provides a single analog output on an analog output line 610. The MUX 606 is operable to selectively sample each of the transducers 602 in accordance with a predetermined scheme. Typically, one of the transducers 602 must have the analog input thereof sampled at a particular time for the purpose of converting it to a digital value and then the next transistor output is sampled. This is facilitated with an analog-to-digital converter 612 (ADC).

In general, the circuitry of the processor 502 is facilitated with the use of conventional chips. In one embodiment, this could utilize a TI MSP430, manufactured by Texas Instruments or a C8051F018/19, manufactured by Silicon Laboratories, among others. These systems provide a mixed signal capability, such that a digital processor can be contained on the same board as data conversion circuitry for converting analog data to digital data and for converting digital data to analog data. The ADC 612 is typically fabricated with a SAR device which utilizes a successive approximation algorithm for the sampling operation. This will typically require a sampling clock and conversion of the analog signal received on the output of the MUX 606 that typically takes at least one conversion cycle to provide a digital signal on the output thereof. Therefore, this conversion cycle is the amount of time required to convert the analog signal on line 610 to a digital value and the amount of time before the next analog line can be sampled.

The output of the ADC 612 is input to a CPU 614. The CPU 614 is a microprocessor or microcontroller based system with an internal or external instruction memory 616. The instruction memory 616 stores instructions for controlling the operation of the CPU 614 and processing of the transducer 602 outputs. Additionally, there will be provided a data memory 618. In the disclosed embodiment, this data memory is a combination of flash nonvolatile memory and RAM volatile memory. The data memory 618 stores parameters and time stamps relating to the outputs of the plurality of transducers 602. The instruction memory 616 may also store data relating to the configuration of the artificial disc 100 components.

The CPU 614 operates in conjunction with an oscillator 620, which may or may not have associated therewith a crystal 622. Depending upon the stability of the oscillator 620, a crystal 622 may not be required. However, for some applications, a fairly stable clock signal is provided. As will be described herein below, the disclosed application requires a real time clock function, which requires the oscillator 620 to have a minimal drift. Therefore, the inclusion of the crystal 622 will provide for this.

The CPU 614 is powered by a power supply 624, which power supply 624, as described herein below, is provided by a battery. However, any type of external power supply could be provided, including an inductively charged capacitor.

For communicating with the CPU 614, there is provided a transceiver 628, which interfaces with the CPU 614 through a serial port interface 630, parallel connection, I2C connection, 1-wire connection Microwire connection, 3-wire connection, etc. such that data can be transferred from the CPU 614 to the transceiver 628 and from the transceiver 628 to the CPU 614. The transceiver 628 interfaces with a wireless link through an antenna 634. The SPI 630 can be any type of serial interconnect. Other types of serial links can be provided, such as the I$^2$C serial bus interface, and RS232 serial bus interface, among others. The transceiver 628 enables interaction of the artificial disc 100 with the external environment in a number of ways, through a wireless link in the disclosed embodiment. The transceiver 628 enables an external source to provide a wake command to the CPU 614 to begin transmission of data stored in the memory 618. Alternatively, the transmission of data stored in the memory 618 may be initiated by the detection of the presence of an inductive coupling mechanism. The transceiver 628 also enables the receipt of commands and firmware updates to the programming at the CPU 614, and enables configuration of devices and trigger levels within the artificial disc 100.

Figure 7:
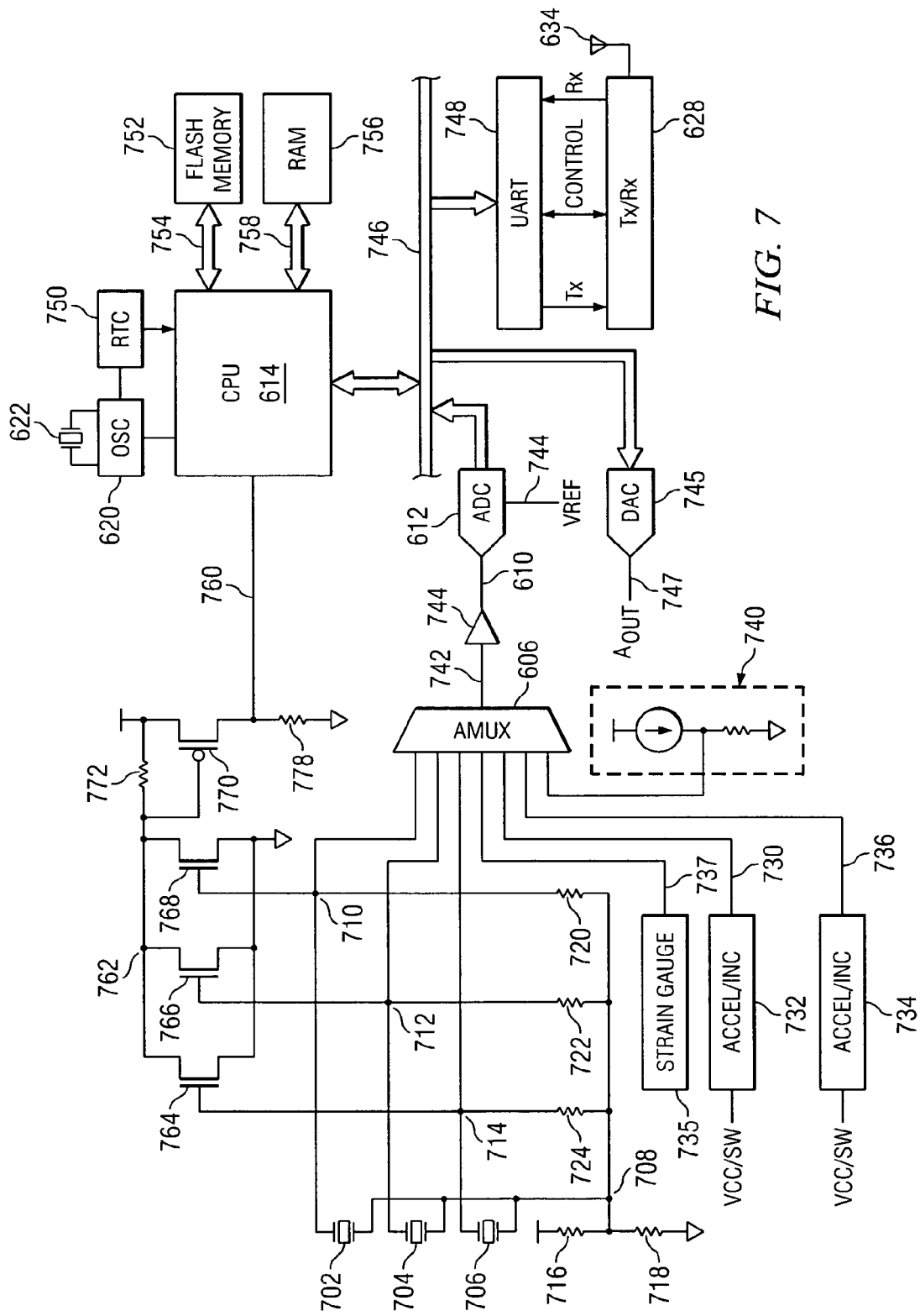
FIG. 7 is a schematic diagram of the electronics of the artificial disc.

Referring now to FIG. 7, there is illustrated a more detailed block diagram of the embodiment of FIG. 6. In the disclosed embodiment, there are provided for the transducer 602 three piezoelectric transducers 702, 704 and 706, as described herein above. Each of the transducers 702-706 is operable to sense force variations to allow force to be dynamically measured in the local area thereof. The transducers 702-706 are dynamic sensors such that they will provide an output when a change occurs in the force on the transducer. Each of the transducers 702-706 has two terminals, one terminal of which is input to a node 708 and the other terminals thereof which are connected to nodes 710, 712 and 714, respectively. Nodes 710-714 are input to three separate inputs of the analog multiplexer 606. Node 708 is connected to a reference voltage which is provided by a resistive divider comprised of a first resistor 716 connected between $V_{DD}$ and node 708 and a second resistor 718 connected between node 708 and ground.

These are high impedance resistors such that variable current flows there through, the ratio typically being set based upon the desired value of the variable current. The current can be changed by any number of configurable triggers including a resistor ladder, digital POT, etc. Then the nodes 710, 712 and 714 are connected to nodes 708 through high impedance resistors 720, 722 and 724, respectively. Thus, the voltage on node 714 will be the signal voltage across the resistor 720-724. For example, if a signal is output by transducer 702, it will be impressed across resistor 720 and there will be a changing voltage on node 710 which will be input to the analog output of the multiplexer 606.

In addition to the three transducers 702-706, there is also provided an analog input on an analog input line 730 to the analog multiplexer 606, which is received from the output of an accelerometer/inclinometer 732. This is a "powered" transducer, which must be connected to the power supply during operation. This is a switched voltage, such that it is disabled during the sleep mode, which will be described herein below. The accelerometer/inclinometer is a device that is operable to measure the angle of inclination along a single axis. Since the inclinometer can only measure tilt along a single axis, a second inclinometer 734 is included, the output thereof connected to the input of the analog multiplexer 606 through an analog line 736. Again, this has a switched power supply input. With the use of the two accelerometer/inclinometers 732 and 734, if they are mounted onto a horizontal plane, rotation of the horizontal plane about the Y-axis or the X-axis can be determined and a "vector" provided or calculated.

One example of an inclinometer which may be used with the system of the present invention includes the device described in U.S. Pat. No. 6,505,409, issued Jan. 14, 2003, which is incorporated herein by reference. The inclinometer described in this patent comprises a spherical shell surrounding a spherical mass and having a reference axis and a plurality of electrodes mounted on the spherical inner surface of the spherical shell. The inclinometer may detect the inclination angle of the reference axis by the output of the plurality of electrodes. The electrodes comprise six electrodes positioned along three orthogonal axes. The electrodes are positioned at points corresponding to a surface of a regular polyhedron. The electrodes are formed as mesh electrodes, each being separated from one another by latitudinal partition lines and longitudinal partition lines. The inclination angle of the reference axis is calculated by using the electrostatic capacity between said spherical mass and the respective electrode. A closed circuit is formed by a contact between said spherical mass and an electrode, and the inclination angle of reference axis is calculated by detecting which electrode forms the closed circuit. Other examples of inclinometers include the VTI SCA610, but any type of inclinometer may potentially be used.

A strain gauge 735 may also provide an analog input to the multiplexor 606 via line 737. This is also a "powered" transducer, which must be connected to $V_{CC}$ during operation. This is a switched voltage that is disabled during the sleep mode. The strain gauge 735 measures the magnitude of the forces applied to the artificial disc 100. The piezoelectric transducers could be used as a wake-up for the strain gauge.

Another input of the analog multiplexer 606 is connected to an internal temperature device 740. This typically utilizes a band-gap generator output, which inherently has a temperature output. Of course, this could be any type of resistor connected in series with a transistor. Thus, the internal temperature can be determined which basically provides the ambient temperature of the chip of the integrated circuit.

The output of the analog multiplexer 606 is connected through an analog line 742 to the input of a programmable amplifier 744, which is an option. This output provides the analog output line 610 which is input to the ADC 612. This ADC 612, in addition to having a sampling clock, also requires a voltage reference, which is typically provided by an external voltage reference on a line 744. The output of the ADC 612 is connected to a digital on-chip bus 746, which interfaces to the CPU 614. Additionally, the digital bus 746 interfaces with an internal UART 748, in the disclosed embodiment, which interfaces with the transceiver 628, as described herein above. This will require a separate data line for transmit data from the UART 748 to the transceiver 628, and a separate line for receive data from the transceiver 628 to the UART 748. There could also be provided control lines for providing control bits such as data ready signals. Digital bus 746 also interfaces with a digital-to-analog converter (DAC) 745, which is operable to provide an analog output on line 747, which can be utilized to control various functions of sensors. The output of the DAC 745 could also be used for configuration or calibration of the transducers or the temperature sensor. A digital output from the CPU 614 may, for example, be used to control a resistor ladder connected to the outputs of the transducers 702, 704, 706. Thus, as the voltage provided by a system battery decreased due to use of charge within the battery, additional resistors from the resistor ladder could be switched into the circuit. This would comprise the programmable wake threshold. The threshold may be programmed from external source (doctors, medical technicians) to meet desired requirements or the threshold may be automatically altered by the CPU if the thresholds are met to many times within a selected time period.

The CPU 614 interfaces with the oscillator 620, which oscillator 620 also interfaces with a real time clock (RTC) function 750. This RTC function 750 is illustrated as a separate function in this embodiment. However, in the disclosed embodiment utilizing the MSP430 integrated circuit, this RTC function is realized with the operation of the CPU 614, where CPU 614 is programmed to count a predetermined number of the output clock cycles of the oscillator 620 corresponding to a second, at which time an internal register is incremented. When the internal register is incremented to a value of 60, it is reset and then a minutes register is incremented. This continues for the hour register, the day register, etc. This is a conventional operation. However, it should be understood that the RTC function can be facilitated with stand alone circuitry that will operate independent of the operation of CPU 614.

In the event that the real time clock function 750 is implemented as separate stand alone circuitry, it should be understood that a separate real time clock implemented in this fashion would not require the use of a separate oscillator 620 to provide the clocking functionalities necessary for operation of the artificial disc 100. This is due to the fact that the real time clock would be operating within a stable temperature environment. Since the real time clock 750 would be located within the body of a patient, the real time clock 750 would always operate within a temperature of approximately 98.6° F.+/−a few degrees for changes in the patient's body temperature. The major factor causing a change in a clock signal is temperature alterations in the operating environment, with power supply variations causing some drift. Since in this configuration the operating environment temperature is substantially unchanged, a reference oscillator signal to continually reconfigure the real time clock 750 is not necessary. Once the internal clock drift is known, the internal RC oscillator may be programmed to account for this drift in all operation.

The CPU 614 also interfaces with a flash memory block 752 through a bus 754 and random access memory (RAM) 756 through a bus 758. However, although illustrated as independent busses 754 and 758, the CPU could interface with the memory 752 and 756 through the bus 746. In actuality, the bus structure is more complex than illustrated in the integrated circuit utilized in the disclosed embodiment.

In order to conserve power, the CPU 614 is enabled to operate in a number of different modes. In one mode, the CPU 614 can operate at a very high frequency, up to 25 MHz. This provides the maximum processing power and processing speed, but also results in the highest current draw. The alternate mode is the low frequency mode wherein the CPU operates on a very low frequency clock, such as 32 KHz. In some applications of the mixed signal integrated circuit, it will go into a sleep mode wherein processing will still be facilitated, but at a much lower rate, with a number of the non-essential functions thereof powered down. In this embodiment, power is of maximum concern with the processing speed or requirements being very low. Thus, the operating speed can always be set at the low clock rate of around 32 KHz. At this clock rate, the CPU 614 is operable to control the ADC 612 to sample data at predetermined times, collect this data, subject it to processing, as will be described herein below, and store this data in flash memory, this flash memory 752 being non-volatile memory. In the third mode, the CPU 614 is placed in a total sleep mode wherein only essential processing is performed. This is a power-down mode wherein all of the current operating instructions, i.e., the state of the CPU 614, are stored in a sleep register. The CPU 614 will have watchdog circuitry associated therewith that will monitor the status of various interrupt inputs. There is provided a single interrupt input 760 in this disclosed embodiment, which is operable to be activated in the event that any signal is generated by any of the transducers 702-706, the sensors basically being zero power sensors.

The interrupt is generated by sensing the signal on nodes 710-714 and Wire-ORing the outputs to a node 762. In order to do this, three n-channel FET transistors 764, 766 and 768 are provided having the gates thereof connected to nodes 714, 712 and 710, respectively, and the source/drain paths thereof connected between ground and the node 762. Node 762 drives the gate of a p-channel FET transistor 770, node 762 connected to $V_{CC}$ through a resistor 772 and the source/drain path of transistor 770 connected between $V_{CC}$ and an interrupt line on the microcontroller. Therefore, the node 762 will be at a voltage such that n-channel transistor 770 is on. This requires the voltage on node 762 to provide a bias voltage that is sufficiently high enough to maintain the n-channel transistors 764-766 off until a signal is generated on the respective nodes 710-714. When one signal goes high, then the associated one of the transistors 764-768 will turn on, pulling node 62 low and turning off transistor 770, raising the voltage on the negative input on line 774. This will generate the interrupt. The advantage of this interrupt circuitry arises in the fact that the circuit does not draw any current when it is not actively generating the interrupt signal. Current is only drawn by the circuit in response to outputs from the transducers. In this fashion, power may be conserved by not utilizing a circuit requiring a constant current draw.

Figure 8:
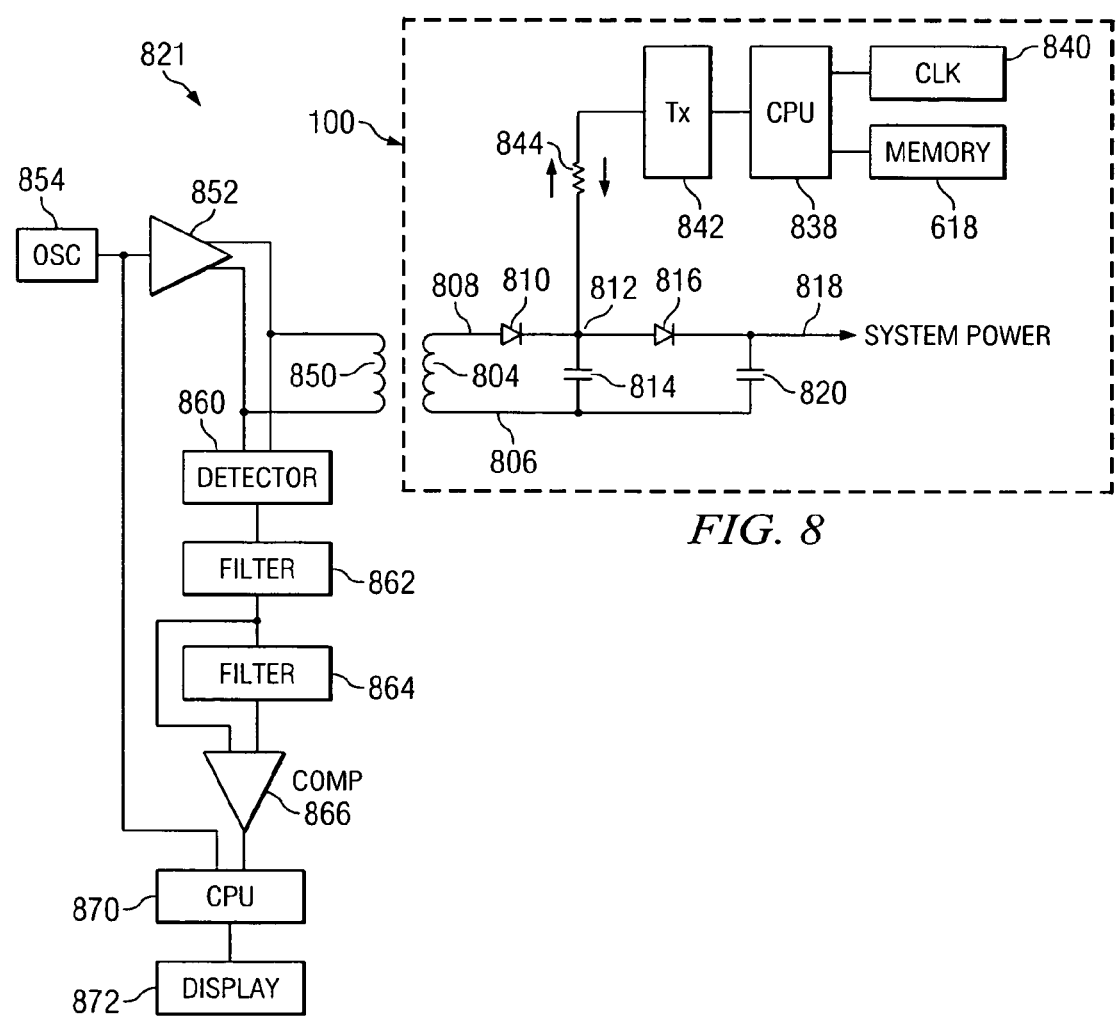
FIG. 8 illustrates the transceiver circuitry for transmitting data from the artificial disc to an external location.

Referring now to FIG. 8, there is illustrated one manner of implementing the transceiver circuitry 628 and antenna 634 utilized for uploading data from the artificial disc 100 to an external processing source 825. The illustrated embodiment of FIG. 8 is that associated with a "passive" system, which refers to the fact that there is no battery associated therewith. In order to operate the system, there is provided an inductive coupling element 804 in the form of an inductor, which is operable to pick up an alternating wave or impulse via inductive coupling and extracting energy therein for storage in the inductive element 804. This will create a voltage across the inductive element 804 between a terminal 806 and the terminal 808. A diode 810 is connected between the node 808 and a node 812 with the anode of diode 810 connected to node 808 and the cathode of diode 810 connected to node 812. Typically, the diode 810 will be fabricated as a schottky diode, but can be a simple P-N semiconductor diode. For the purposes of this embodiment, the P-N diode will be described, although it should be understood that a schottky diode could easily be fabricated to replace diode 810. The reason for utilizing a schottky diode is that the schottky diode has a lower voltage drop in the forward conducting direction.

The diode 810 is operable to rectify the voltage across the inductive element 804 onto the node 812 which has a capacitor 814 disposed between node 812 and node 806. Node 812 is also connected through a diode 816 having the anode thereof connected to node 812 and the cathode thereof connected to node 818 to charge up a capacitor 820 disposed between node 812 and 806. The capacitor 820 is the power supply capacitor for providing power to the system.

The CPU 614 and the clock circuit 750 are provided for processing and timing functions to the system. A memory 839 is provided in communication with the CPU 614 for storage of an ID unique to the system to allow the CPU 614 to retrieve this information for transmittal back to the external processing source 820. This retrieval is automatic when the system is powered up and is continuous as long as the system is powered. This memory 618 is nonvolatile, such as a RAM, or it could be a programmable nonvolatile memory, such as flash memory.

In order to communicate with the CPU 614 for transferring data therefrom, a transmit circuit 628 is provided for interfacing to node 812 through a resistive element 844. This allows energy to be transmitted to node 812. It is important to note that the semiconductor junction across diode 810 is a capacitive junction. Therefore, this will allow coupling from node 812 to node 804. Although not illustrated, this could actually be a tuned circuit, by selecting the value of the capacitance inherent in the design of the diode 810. In any event, this allows an RF connection to be provided across diode 810 while allowing sufficient energy to be input across inductive element 804 to provide a voltage there across for rectification by diode 810 and capacitor 814. Typically, the frequency of this connection will be in the megahertz range, depending upon the design. However, many designs could be utilized. Some of these are illustrated in U.S. Pat. No. 4,333,072 by Beigel, entitled "Identification Device" issued Jun. 1, 1982 and U.S. Pat. No. 3,944,982 by Mogi et al., entitled "Remote Control System for Electric Apparatus" issued Mar. 6, 1982, both of which are hereby incorporated by reference. With these types of systems, power can be continually provided to the node 812 and subsequently to capacitors 814 and 820 to allow power to be constantly applied to the system.

The external processing source 820 includes an inductive element 850 which is operable to be disposed in an area proximate to the artificial disc. The inductive element 850 is driven by a driving circuit 852 which provides a differential output that is driven by an oscillator 854. This will be at a predetermined frequency and power level necessary to couple energy from inductive element 850 to inductive element 804. Since the external processing source 820 is an external system, the power of the oscillator 854 can be set to a level to account for any losses encountered in the scanning operation.

When the information is received from the artificial disc, it is superimposed upon the oscillator signal driving the inductive element 850. This is extracted therefrom via a detector 860 which has the output thereof input to a first low pass filter 862 and then to a second low pass filter 864. The output of low pass filters 862 and 864 are compared with a comparator 866 to provide the data. The filter 862 will provide an average voltage output, whereas the filter 864 will provide the actual digital voltage output. The output of the comparator 866 is then input to a CPU 870 which is powered by the oscillator 854 to process the data received therefrom. This can be input to a display 872.

Figure 8A:
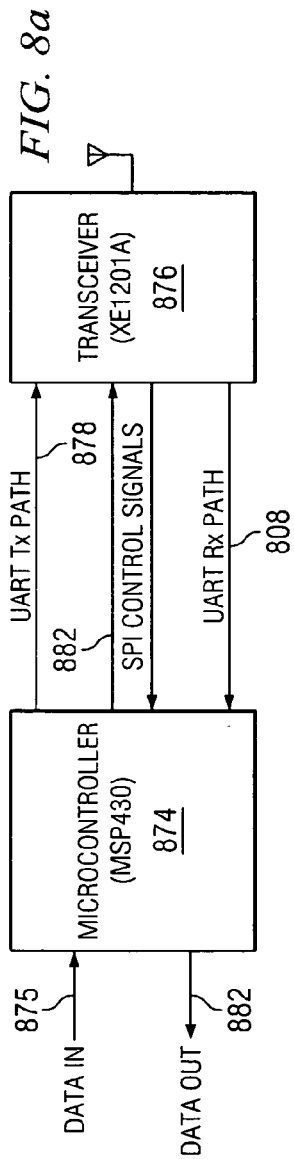
FIG. 8a illustrates a wireless digital full duplex RF transceiver for transmitting data from the artificial disc to an external location.

Referring now to FIG. 8a there is illustrated a wireless digital full duplex transceiver part number XE1201A by Xemics. A microcontroller 874 receives data from an input port 875. The microcontroller 875 includes an 8-bit ADC which samples the input data at a rate of 16 KHz. The ADC pushes each sample into an ADC FIFO buffer. A algorithm pulls these samples from the FIFO buffer and using a continuously bearing slope delta compression scheme compresses each 10-bit sample to a single bit. Several consecutive samples are combined to form a frame of data that can be transmitted by the microcontroller's UART. A CRC may be used to verify data. Data is pushed onto a UART transmit FIFO buffer. The UART transmits data to and from an RF transceiver 876 over UART transceiver path 878. The SPI peripheral is used to control transceiver settings during transmission and reception over SPI control signal lines 882. The transmitting and receiving RF transceivers are synchronized so that the two transceivers do not try to transmit simultaneously. This is achieved by implementing transmission state machines in the software controlling the transceiver 876. After RF transmission, the controller 874 receiving data stores the data in a UART receive FIFO buffer. Data is pulled from this FIFO buffer by a decompression algorithm that converts each byte of received data to 8-bit DAC output values. Each pair of output values is averaged to minimize noise, so the decompression algorithm outputs four DAC samples per UART data byte. Recovered data samples are pushed onto the DAC output FIFO buffer, and the samples from the buffer are output over the data out port 882.

Figure 9:
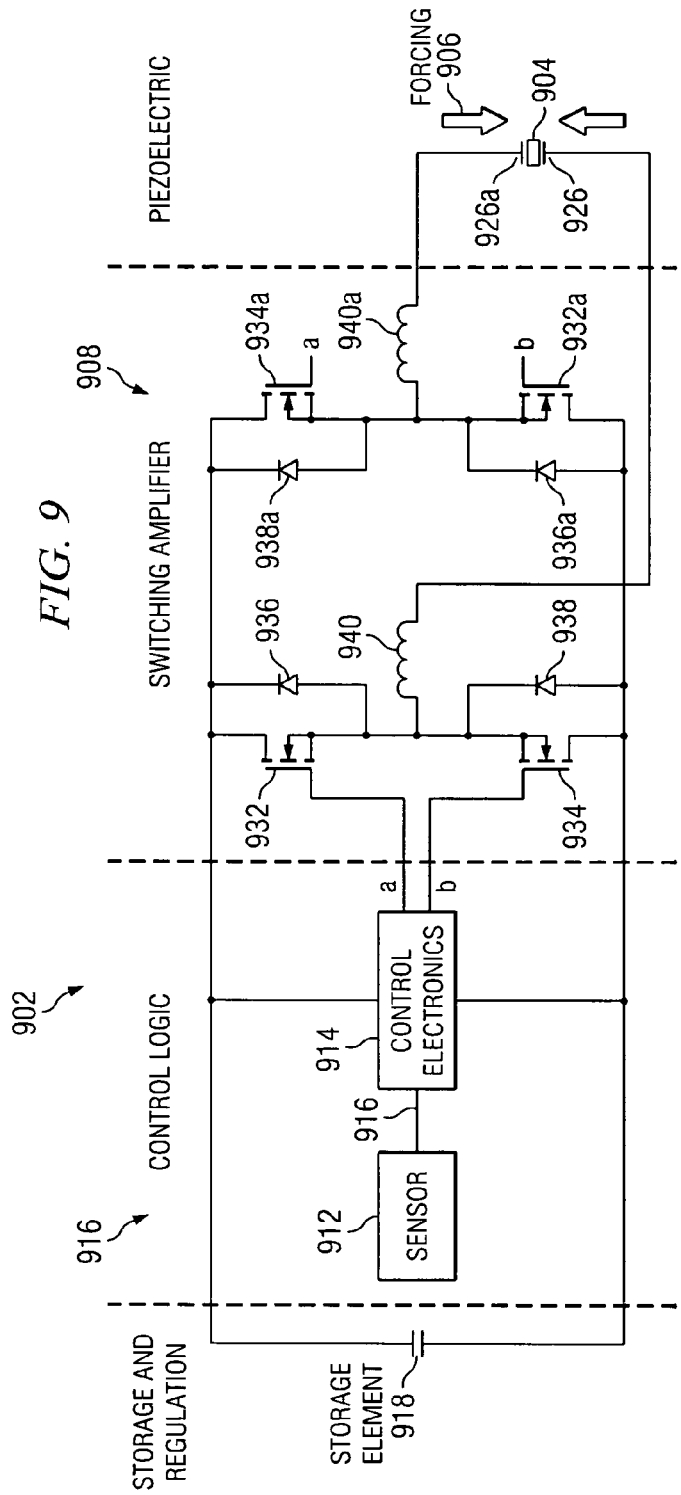
FIG. 9 is a circuit diagram of a piezoelectric generator for powering an artificial disc.

Referring now to FIG. 9, there is illustrated a piezoelectric generator circuit which may be used to power the artificial disc 100. FIG. 9 illustrates an electronic circuit 902 for extracting electric power from a transducer 904 acted upon by a disturbance 906. The electronic circuit includes amplifier electronics 908. Amplifier electronics 908 includes an H-bridge switching amplifier 915. In a first approach, control logic 918 operates MOSFETs 932, 932a together, and MOSFETs 934, 934a together:

Phase I

MOSFETs 932, 932a are off, MOSFETs 934, 934a are turned on, current flows through MOSFETs 934, 934a, and energy from transducer 904 is stored in inductors 940, 940a.

Phase II

MOSFETs 934, 934a are turned off and MOSFETs 932, 932a are switched on, current flows through diodes 936, 936a, and the energy stored in inductors 940, 940a is transferred to storage element 918.

Phase III

As the current becomes negative, the current stops flowing through diodes 936, 936a and flows through MOSFETs 932, 932a, and energy from storage element 918 is transferred to inductors 940, 940a.

Phase IV

MOSFETs 932, 932a are turned off, current flowing through diodes 938, 938a increases, and the energy stored in inductors 940, 940a is transferred to transducer 904.

In a second operational approach, only half of the H-bridge is operated at any given time, depending upon the polarity of the voltage desired on transducer 906. When a positive voltage is desired, MOSFET 934a is turned off and MOSFET 932a is tuned on, grounding side 926a of transducer 904. MOSFETs 932 and 934 are then turned on and off to affect the voltage on side 926 of transducer 904. When a negative voltage on transducer 904 is desired, MOSFET 932 is turned off and MOSFET 934 is turned on, grounding side 926 of transducer 904. MOSFETs 932a and 934a are then turned on and off to affect the voltage on side 926a of transducer 904.

Control logic 910 includes a sensor 912, for example, a strain gauge, micro pressure sensor, PVDF film, accelerometer, or active fiber composite sensor, which measures the motion or some other property of disturbance 906, and control electronics 914. Sensor 912 supplies a sensor signal 916 to control electronics 914. Sensor 912 can measure a number of properties including, for example, vibration amplitude, vibration mode, physical strain, position, displacement, electrical or mechanical state such as force, pressure, voltage, or current, and any combination thereof or rate of change of these, as well as temperature, humidity, altitude, or air speed orientation. In general, any physically measurable quantity which corresponds to a mechanical or electrical property of the system. A storage element 918 is used for storing the energy generated by the disturbance 906 and may comprise a rechargeable battery, capacitor, or a combination thereof. Amplifier electronics 920 provides for flow of electrical power from transducer 904 to storage element 918, as well as from storage element 918 to transducer 904.

Figure 10:
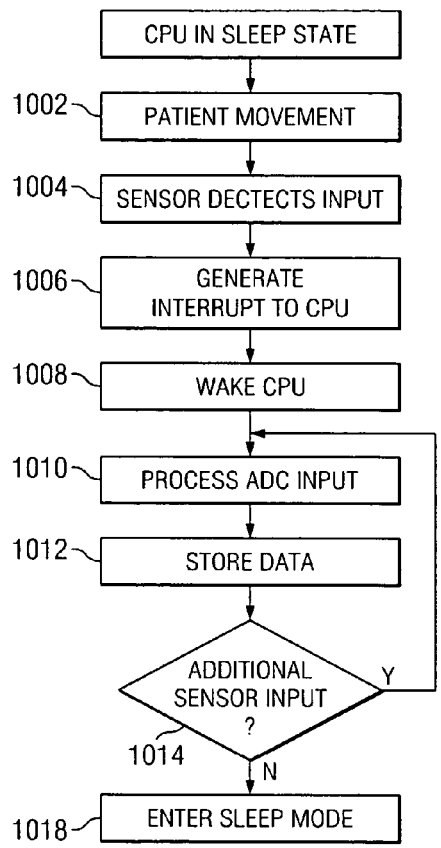
FIG. 10 is a flow diagram illustrating the manner in which the central processing unit is awakened from a sleep mode to store data.

Referring now to FIG. 10, there is illustrated a flow diagram describing the manner in which the transducers 202 may generate an input to awaken the central processing unit 502 from a sleep mode. Initially, at step 1000, the central processing unit 502 has powered down to a sleep mode in order to conserve energy within the artificial disc 100. Patient movement is detected at step 1002 and generates an input to the transducers 202 that is detected by the transducers at step 1004. Outputs of the transducers 202 cause the generation, at step 1006, of an interrupt signal to the central processing unit 502. The interrupt signal is created utilizing the three n-channel transistors and one p-channel transistor described in FIG. 7. The interrupt signal from the p-channel transistor causes the CPU 614 to awaken from the sleep mode at step 1008. Once the CPU 614 awakens, it begins processing the output of the ADC at step 1010. The manner in which the data is processed will be more fully discussed in a moment with respect to FIGS. 11 and 12.

Processing by the central processing unit of the ADC output generates a number of parameters which are stored at step 1012 within the memory of the artificial disc. Once the data has been stored, inquiry step 1014 determines if additional input is being received from the transducers. If so, control passes back to step 1010, and the ADC output is again processed for storage within the memory. If no additional transducer input is being received, the central processing unit determines, at step 1016, whether the time out period for return to the sleep mode has expired. If not, the central processing unit re-enters, at step 1018, the sleep mode to conserve system power.

Figure 11:
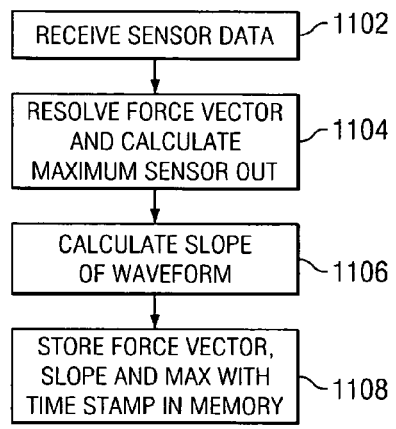
FIG. 11 is a flow diagram illustrating the manner in which the central processing unit processes received sensor data to store transducer output parameters and associated time stamps in memory.

Referring now to FIG. 11, there is illustrated a flow diagram describing the manner in which the central processing unit processes the received ADC output. The transducer data is received, at step 1102, from the ADC at the central processing unit. Using the received data, the central processing unit resolves a single resultant force vector and calculates the maximum output value of the transducer waveform at step 1104. The central processing unit next calculates, at step 1106, the slope of the transducer waveform. Finally, the resolved resultant force vector and calculated slope and maximum value parameters are stored in memory at step 1108 with a time stamp indicating the point in real time at which the transducer waveform was received from the transducer. By storing only selected parameters describing the waveform output rather than the entire waveform output much less memory space is required within the artificial disc 100. It should be noted that all samples of the data could be stored for later transmission or processed to further reduce the information to dynamic vectors. The more reduced the dataset, the lower the power requirements to transfer the data.

Figure 12:
FIG. 12 illustrates the manner in which parameters and associated time stamps are stored in memory.

Referring now to FIG. 12, there is provided an illustration of the manner in which various parameters may be stored with associated time stamps 1204 as described in FIG. 10. The memory associated with the central processing unit contains a number of storage locations 1206 for storing parameters related to transducer inputs received when the CPU is awakened from sleep mode as described with respect to FIG. 10. These parameters are stored within a parameter field 1202 of the storage location 1006. Associated with each parameter field is a time stamp field 1004 indicating the time and date at which the parameters were generated. As can further been seen in FIG. 12, the parameters may consist of a variety of information including maximum and minimum values for each of the transducers, an x angle value and y angle value and a temperature value. In this manner, a large amount of data with respect to transducer outputs may be stored in system memory by storing a limited number of characteristics rather than the entire transducer waveform. In this fashion, a physician or diagnostician may review the system parameters to determine critical outputs of the transducers and have an idea at what point in time the activities of the patient were creating these critical outputs.

The time stamped parameters stored in the memory may include dynamic data representing the changes in the forces recorded by the transducers 202, temperature data from the temperature sensor 740, tilt and acceleration data from the accelerometers 732,734 and magnitude data from the resistor strain gauge 735.

Figure 13:
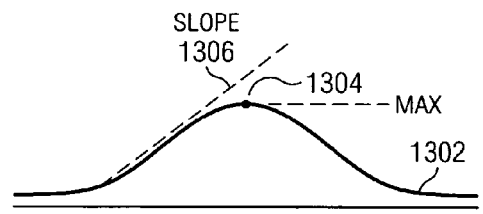
FIG. 13 illustrates the output of a transducer and the slope and max parameters which may be calculated with respect thereto.

Referring now to FIG. 13, there is illustrated the output of a transducers 202*a*-202*c* responsive to movements of the intervertebral disc 100 caused by movement of the patient. The data from the transducers may be stored in a number of fashions. In a first embodiment, a 3D resultant vector is generated from the outputs of each of the transducers. The resultant slope and magnitude of the vector may then be stored in memory if these values exceed certain predetermined thresholds. If memory storage is limited a determination and deletion of a smallest presently stored resultant vector may be made. This will create space for the storage of characteristics relating to the new larger resultant vector.

In a second embodiment, the entire waveform output from each of the transducers 202*a*-202*c* may be stored in memory for a selected period of time. In this situation the thresholds relating to the occurrence of an event that required the storage of data would have to be set sufficiently high that data was only stored a few times per day. If waveforms were stored too frequently, the memory space would quickly be exhausted and battery power would be depleted.

In a third embodiment, rather than storing the entire output waveform 1302 within the memory 504, the central processing unit 502 generates various characteristics describing the output waveform 1302. These parameters include a maximum value 1304 representing the peak output of the transducer waveform 1302 and the slope value 1306 represents the maximum slope of the output waveform 1302 of the transducer and provides an indication of the intensity of the pressures being placed between the upper plate 106 and lower plate 108 of the artificial disc 100.

Figure 14:
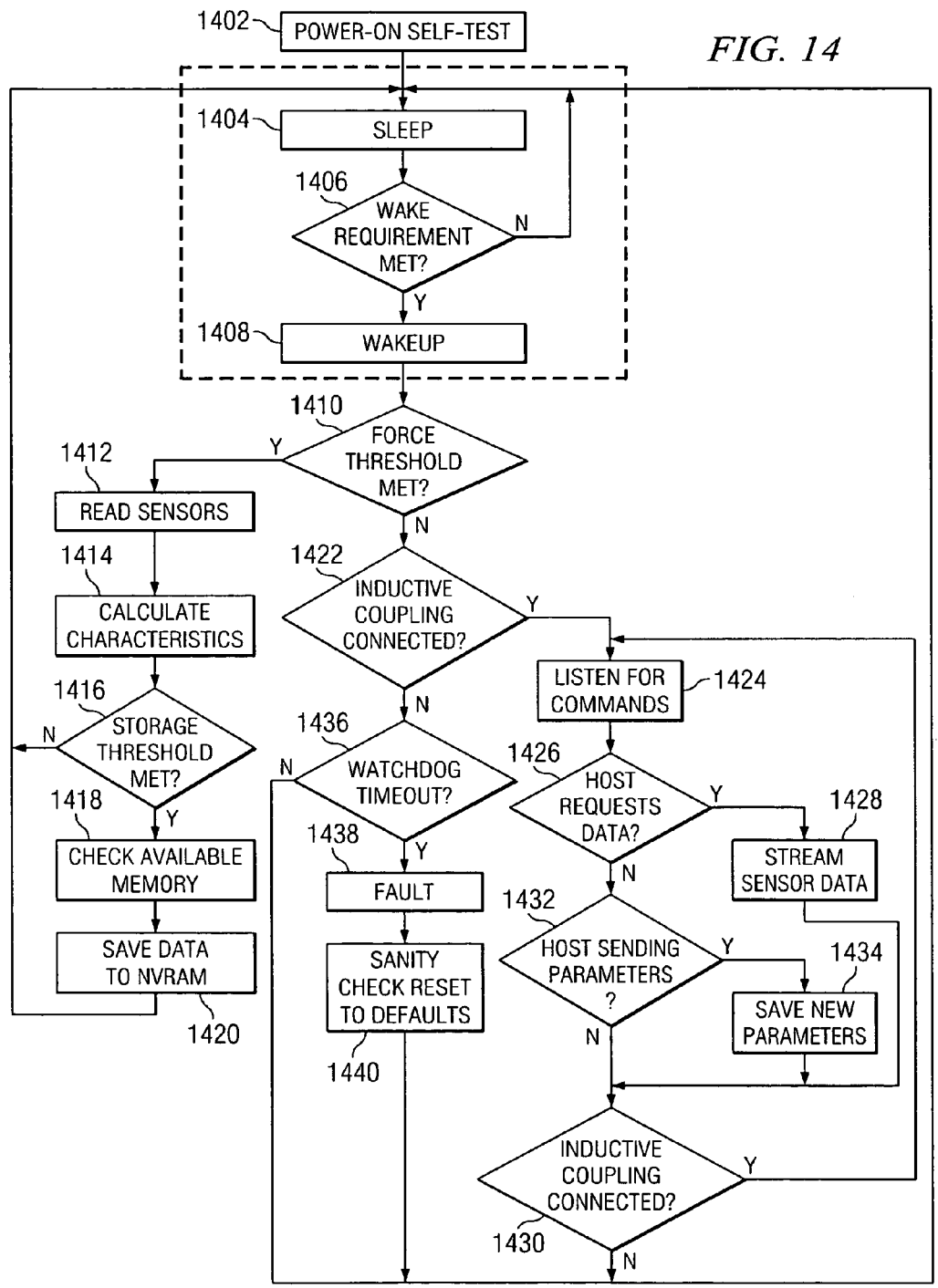
FIG. 14 is a flow diagram illustrating the operation of the central processing unit in both its continuous mode and store mode of operation.

The central processing unit 502 includes two separate modes for transmitting data using its communications link 508 and antenna 510. The operation of these modes are more fully illustrated in the flow diagram of FIG. 14. After occurrence of the power on self test at step 1402, the CPU enters the sleep mode at step 1404. Inquiry step 1406 determines whether or not a waking requirement has been initiated for the sleep mode. If not, control returns back to step 1404. Once a waking requirement has been met, the CPU will be awakened at step 1408.

Inquiry step 1410 determines whether force threshold requirements have been met within the artificial disc 100. If so, data from the sensors is read at step 1412, and characteristics of the provided signals are calculated at step 1408. The force thresholds may be programmed from external source to meet desired requirements or the force thresholds may be automatically altered by the CPU if the thresholds are met to many times within a selected time period. Inquiry step 1416 determines whether storage threshold requirements have been met, and if not, the CPU will return to the sleep mode at step 1404. If storage threshold requirements are met, the available memory is checked at step 1418, and the data is saved to memory at step 1420. Once the data has been saved, the CPU can return to the sleep mode at step 1404.

If the force threshold requirements have not been met at inquiry step 1410, inquiry step 1422 determines whether there is any inductive coupling connected. If so, the CPU will listen for commands at step 1424. Upon hearing commands, the CPU determines at inquiry step 1426 whether the host has requested data. If so, a stream of sensor data is provided to the host at step 1428. Inquiry step 1430 determines whether the inductive coupling is still connected, and if so, control will return back to step 1424 to listen for additional commands. If the inductive coupling is not connected, the CPU will return to the sleep mode at step 1404.

If the host has not requested data, inquiry step 1432 determines whether the host is sending parameters. If so, the new parameters are saved at step 1434 and control passes back to inquiry step 1430 to determine if inductive coupling remains connected. If the host is not transmitting parameters, control will pass to inquiry step 1430 to again determine if the inductive coupling is connected.

If no inductive coupling is detected at inquiry step 1422, inquiry step 1436 determines whether a watchdog timeout has occurred. If so, a fault is issued at step 1438 and a sanity check is reset to the default at step 1440. The CPU will then return to the sleep mode at step 1404. If no watchdog timeout is detected at inquiry step 1436, the CPU will then return to the sleep mode at step 1404.

Figure 15:
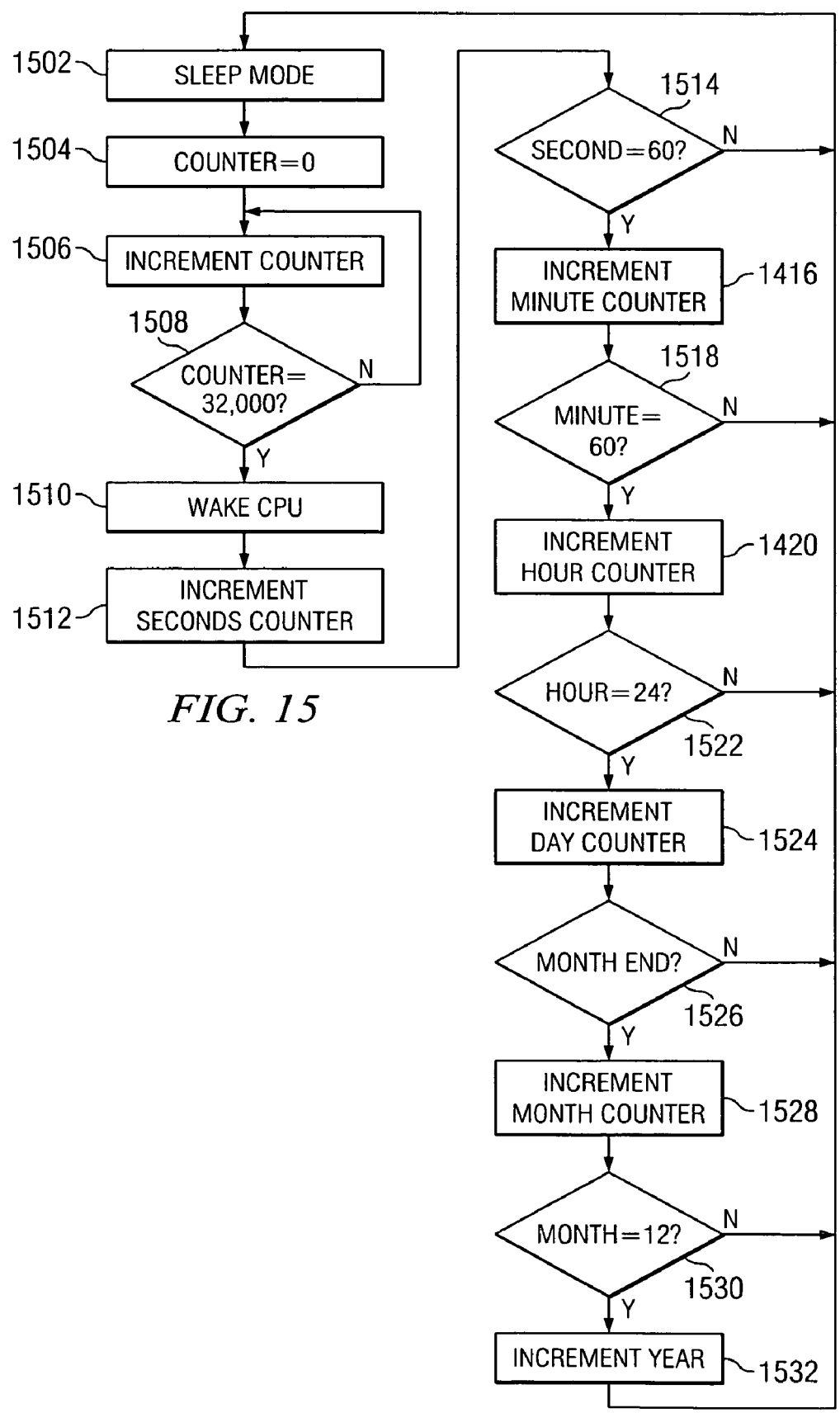
FIG. 15 is a flow diagram illustrating the manner in which the artificial disc tracks time while conserving system power by having the CPU remain in a sleep mode.

Referring now to FIG. 15, there is illustrated the manner in which the real time clock 750 associated with the CPU 614 is able to track time within the artificial disc 100 while allowing the CPU 614 to conserve power by remaining in the sleep mode for a large percentage of the time in order to extend battery life. The CPU 614 is initially in the sleep mode at step 1502. A counter is set to "0" at step 1504. The counter is incremented, at step 1506, in response to the execution of one clock cycle of the real time clock which is running at 32 KHz per second. Inquiry step 1508 determines if the counter counting the clock cycles of the real time clock has reached 32,768.

If not, control passes back to step 1506 wherein the counter is again incremented by one. If inquiry step 1508 determines that the counter does equal 32,768, the CPU 614 is awakened from sleep mode at step 1510. A "seconds" counter is incremented at step 1512, and inquiry step 1514 determines whether the "seconds" counter equals 60. If the "seconds" counter does not equal 60, the CPU 614 returns to sleep mode at step 1502 to conserve power. If inquiry step 1514 determines that the "seconds" counter equals 60 the "minutes" counter is incremented at step 1516. Inquiry step 1518 determines whether the "minutes" counter is equal to 60. If the "minutes" counter does not equal to 60, control returns to step 1502 and the CPU 614 re-enters the sleep mode. If the "minutes" counter equals 60, an "hour" counter is incremented at step 1520. Responsive to incrementing of the "hour" counter, inquiry step 1522 determines whether the "hour" counter equals 24. If not, the CPU 614 re-enters the sleep mode at step 1502. When the "hour" counter equals 24, a "day" counter is incremented at step 1524. Inquiry step 1526 determines if the end of the presently counted month has been reached. The month end number will, of course, vary depending upon the month of the year the counter is presently tracking. If the end of the month has not been reached, the CPU 614 re-enters the sleep mode at step 1502. Otherwise, the "month" counter is incremented at step 1528 and inquiry step 1530 determines whether the "month" counter is equal to 12. If the "month" counter does not equal 12, the CPU 614 re-enters the sleep mode to conserve power at step 1502. If inquiry step 1530 determines that the "month" counter equals 12, the "year" is incremented within the CPU 614 at step 1532, and the CPU re-enters the sleep mode at step 1502. Using this process, the real time clock 750 may keep track of time using the 32 KHz clock signal and conserve system power by allowing the CPU 614 to remain in sleep mode until it is necessary to increment the seconds, minutes, hours, days, month and year counters.

Figure 16:
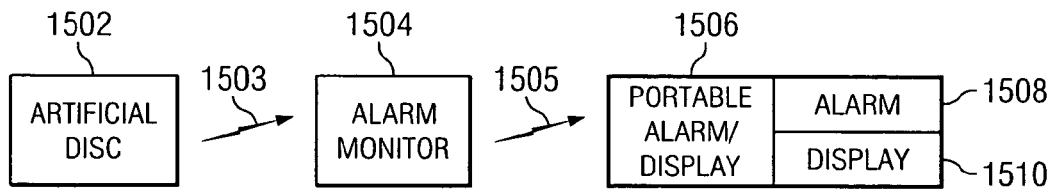
FIG. 16 is a block diagram illustrating a particular use of the artificial disc with an alarm monitoring system.

Referring now to FIG. 16, there is illustrated a particular application of the artificial disc 100 with respect to generating alarms to warn a patient of conditions which may be harming their spine or prosthesis. The embodiment consists of the artificial disc 1602 as described herein above. The artificial disc 1602 interfaces with a monitor alarm 1604. The monitor alarm 1604 would be strapped to a patient's back in close proximity to the artificial disc 1602 on the exterior of the patient's body such that the artificial disc 1602 and alarm monitor 1604 could inductively communicate via a link 1603 in the manner described with respect to the FIG. 8 via an inductive coupling interface. The alarm monitor 1604 also includes an RF interface for generating an RF link 1605 with a portable alarm/display 1606 worn, for example, on the wrist of the patient. The RF link 1605 is established between the alarm monitor 1604 and portable alarm/display 1606 using any known short range RF technology. The portable alarm/display 1606 would include an alarm portion 1608 for generating an audio or visual alarm to the patient and a display 1610 for displaying information indicative of the problem. The CPU 614 of the artificial disc 1602 would be programmed to generate and transmit alarm signals to the alarm monitor in response to forces measured by the transducers within the artificial disc 1602 exceeding predetermined limits. These predetermined limits would be established as indicating excessive load applied to the patient's spine or prosthesis. These limits can be changed periodically by external program signals, or a program schedule can be stored to automatically change over time.

Figure 17:
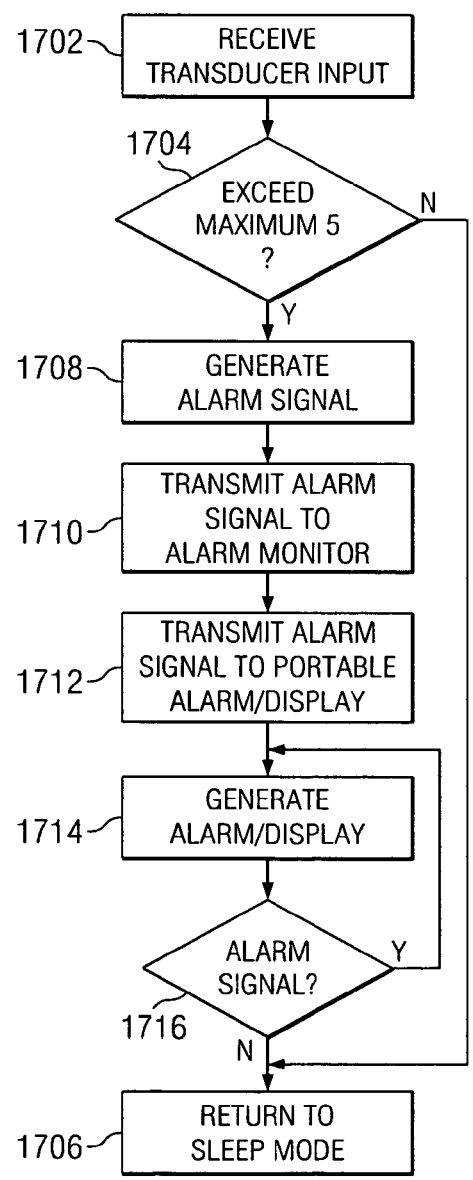
FIG. 17 is a flow diagram illustrating the operation of the artificial disc with the alarm monitoring system.

Referring now to FIG. 17, there is illustrated a flow diagram describing the operation of the embodiment illustrated in FIG. 16. The CPU 614 is awakened from its sleep mode, as described previously with respect to FIG. 10, when it receives transducer input at step 1702. Inquiry step 1704 determines whether the inputs received from the transducers indicate that the patient has exceeded certain predetermined maximums. If not, the CPU 614 will return to the sleep mode at step 1706 and no alarm is generated. If the received transducer inputs indicate that the predetermined maximums have been exceeded, an alarm signal is generated by the CPU at step 1708. The alarm signal and any data received from the transducers indicating the condition raising the alarm is transmitted to the alarm monitor at step 1710. The alarm monitor 1604 transmits the alarm signal and any associated data to the portable alarm/display at step 1712. The portable alarm/display 1606 generates any applicable alarms or displays at step 1714 required to inform the patient of the alarm condition. Inquiry step 1716 determines if an alarm signal is still being received from the alarm monitor at step 1604. If so, the portable alarm/display 1606 continues to generate the alarm and display information at step 1714. Once the alarm signals ceases to be received, the CPU 614 will return to the sleep mode at step 1706.

Although the preferred embodiment has been described in detail, it should be understood that various changes, substitutions and alterations can be made therein without departing from the spirit and scope of the invention as defined by the appended claims.

What is claimed is:

1. A prosthetic implant for implanting in a body, the implant comprising:
   a support member for interfacing with bone;
   at least one sensor for measuring parameters associated with the prosthetic implant;
   a memory for storing an output of the at least one sensor for later retrieval;
   a power management device for controlling operation of said memory, said power management device operable to apply operating power to said memory when storing information therein and retrieving information therefrom, and said power management device operable to reduce power applied to said memory device at times when information is not being stored therein or retrieved therefrom; and
   a telemetry device operable to transmit at least some contents of said memory in response to an external request.

2. The prosthetic implant of claim 1, wherein said support member is adapted to adhere to said bone.

3. The prosthetic implant of claim 1, wherein said support member includes a first interface surface for interfacing with bone on one side of an articulating joint and a second interface surface for interfacing with bone on another side of the articulating joint, and said sensor disposed proximate to one of said first or second interface surfaces.

4. The prosthetic implant of claim 3, wherein said memory is disposed between said first and second interface surfaces.

5. The prosthetic implant of claim 3, wherein said first and second interface surfaces are associated with first and second support structures formed of a first material, and further comprising a third support structure disposed between said first and second support structures and comprising a second material different from said first material.

6. The prosthetic implant of claim 5, wherein said second material is a resilient material and said first material is a non-resilient material.

7. The prosthetic implant of claim 6, wherein said sensor is disposed on a surface of one of said first and second support structures facing an interface therewith of said third support structure.

8. The prosthetic implant of claim 1, wherein the prosthetic implant is an implantable vertebral disk.

9. The prosthetic implant of claim 1, and further comprising a power source for powering said memory.

10. The prosthetic implant of claim 9, wherein said telemetry device is powered by said power source.

11. The prosthetic implant of claim 1, wherein said power management device includes:
an activity detector for detecting a change in an output of said sensor; and
a power switch for selectively applying power to said memory in response to said activity detector detecting a change in the output of said sensor that exceeds a predetermined threshold.

12. The method of claim 11, further comprising a processing unit, said processing unit controlling the placing of information in said memory and the retrieval of information therefrom, said processing unit having the power thereto controlled by said power management device, such that power thereto can be decreased when information is not being placed in said memory or being retrieved therefrom.

13. The prosthetic implant of claim 12, wherein said processing unit, when operating in a reduced power mode, is operable to control said power switch and is operable to process the output of said activity detector.

14. The prosthetic implant of claim 1, wherein the at least one sensor measures at least one force associated with said support member.

15. The prosthetic implant of claim 1, wherein the at least one sensor measures an inclination associated with said support member.

16. The prosthetic implant of claim 1, wherein the at least one sensor measures a temperature associated with said support member.

17. A prosthetic implant for implanting in a body, the implant comprising:
a support member for interfacing with bone;
at least one sensor for measuring parameters associated with the prosthetic implant and providing an output signal representative thereof;
a processing unit for receiving the output of said at least one sensor and processing said received output; and
a memory for storing information representative of the output of said at least one sensor under control of said processing unit;
an activity detector for detecting a change in the output of said sensor; and
a power switch for selectively applying power to said memory in response to said activity detector detecting a change in the output of said sensor that exceeds a predetermined threshold and for causing said processing unit to operate in a reduced power mode when the predetermined threshold output of said sensor is not exceeded for a predetermined period of time.

18. The prosthetic implant of claim 17, wherein said memory comprises a non-volatile memory which is controlled by said power management device to apply power to said memory at least during placing of information therein and to reduce power thereto during at least a portion of the time that said processing unit operates in reduced power mode.

19. The prosthetic implant of claim 17, and further comprising a telemetry device operable to transmit at least some contents of said memory in response to an external request.

20. The prosthetic implant of claim 19, wherein said power management device is operable to apply power to said telemetry device when information is transferred by said telemetry device.

21. The prosthetic implant of claim 19, wherein said telemetry device is operable to receive information from an external device for storage in said memory.

22. The prosthetic implant of claim 19, wherein said telemetry device is operable to receive information from an external device to define an end of a reduced power time period during which said processing unit operates in a reduced power mode.

23. The prosthetic implant of claim 17, wherein the predetermined threshold is selectively programmable.

24. The prosthetic implant of claim 17, wherein the predetermined threshold is automatically altered responsive to the sensor exceeding the predetermined threshold a predetermined number of times in a second predetermined time period.

25. The prosthetic implant of claim 17, wherein said processing unit, when operating in said reduced power mode, is operable to control said power switch and is operable to process the output of said activity detector.

26. The prosthetic implant of claim 17, wherein said activity detector is non power consuming at least prior to any detection of activity from said sensor.

27. The prosthetic implant of claim 17, wherein said support member is adhered to said bone.

28. The prosthetic implant of claim 17, wherein said support member includes a first interface surface for interfacing with bone on one side of an articulating joint and a second interface surface for interfacing with bone on another side of the articulating joint, and said sensor disposed proximate to one of said first or second interface surfaces.

29. The prosthetic implant of claim 28, wherein said processing unit is disposed between said first and second interface surfaces.

30. The prosthetic implant of claim 28, wherein said first and second interface surfaces are associated with first and second support structures formed of a first material, and further comprising a third support structure disposed between said first and second support structures and comprised of a second material different from said first material.

31. The prosthetic implant of claim 30, wherein said second material is a resilient material and said first material is a non-resilient material.

32. The prosthetic implant of claim 31, wherein said sensor is disposed on the surface of one of said first and second support structures facing the interface therewith of said third support structure.

33. The prosthetic implant of claim 17, wherein the prosthetic implant is an implantable vertebral disk.

34. The prosthetic implant of claim 17, wherein said sensor comprises a dynamic force sensor.

35. The prosthetic implant of claim 34, wherein said dynamic force sensor comprises a piezoelectric sensor.

36. The prosthetic implant of claim 17, wherein said power management device is operable to place said processing unit in a non-reduced power mode at times other than said predetermined time periods such that said processing unit can process the information output by said sensor in said non-reduced power mode.

37. The prosthetic implant of claim 17, wherein the at least one sensor measures at least one force associated with said support member.

38. The prosthetic implant of claim 17, wherein the at least one sensor is operable to measure an inclination associated with said support member.

39. The prosthetic implant of claim 17, wherein the at least one sensor measures a temperature associated with said support member.

40. An implant for use within a body proximate to a particular location, comprising:
- at least one sensor for measuring parameters associated with the particular location;
- a time base for providing temporal information;
- a memory for retrievably storing the output of the at least one sensor in association with the temporal information wherein said memory is a non-volatile memory;
- a power management device for controlling operation of said memory, said power management device operable to apply power to said memory when placing information therein and retrieving information therefrom, and said power management device operable to reduce power applied to said memory at times when information is not being stored therein or retrieved therefrom; and
- a telemetry device operable to transmit the at least some contents of said memory in response to an external request.

41. The implant of claim 40, further comprising a power source for powering said memory.

42. The implant of claim 41, wherein said telemetry device is powered by said power source.

43. The implant of claim 40, wherein said power management device includes:
- an activity detector for detecting a change in the output of said sensor; and
- a power switch for selectively applying power to said memory in response to said activity detector detecting a change in the output of said sensor that exceeds a predetermined threshold.

44. The implant of claim 43, further comprising a processing unit powered by said power source, said processing unit controlling the placing of information into said memory and the retrieval of information therefrom, said processing unit having the power applied thereto controlled by said power management device, such that power thereto applied to the processing unit can be decreased when information is not being placed into said memory or being retrieved therefrom.

45. The implant of claim 44, wherein said processing unit, when operating in a reduced power mode is operable to control said power switch and is operable to process the output of said activity detector.

46. The implant of claim 40, wherein the at least one sensor measures temperature of the body proximate to the particular location.

47. A prosthetic implant system, the system comprising:
- a prosthetic spinal disc having a sensor for measuring a parameter associated with the prosthetic spinal disc and a transmitter suitable to transmit data related to the measured parameter;
- an alarm monitor for receiving the transmitted data and for generating an alarm upon meeting of a predetermined criterion;
- an activity detector for detecting a change in the output of said sensor; and
- a power switch for selectively applying power to said memory in response to said activity detector detecting a change in the output of said sensor that exceeds a predetermined threshold.

* * * * *